United States Patent
Nagai et al.

(10) Patent No.: US 9,978,163 B2
(45) Date of Patent: May 22, 2018

(54) EXPOSURE MANAGEMENT SYSTEM

(71) Applicant: Toshiba Medical Systems Corporation, Otawara-shi (JP)

(72) Inventors: Seiichirou Nagai, Otawara (JP); Yasuhiro Sugawara, Nasushiobara (JP); Atsushi Kotani, Nasushiobara (JP); Tsutomu Ichikawa, Yokohama (JP); Toshikatsu Oohashi, Otawara (JP); Shoji Yashiro, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 193 days.

(21) Appl. No.: 14/795,035

(22) Filed: Jul. 9, 2015

(65) Prior Publication Data

US 2016/0021727 A1  Jan. 21, 2016

(30) Foreign Application Priority Data

Jul. 17, 2014  (JP) .................................. 2014-147041

(51) Int. Cl.
*H05G 1/64* (2006.01)
*G06T 11/20* (2006.01)
(Continued)

(52) U.S. Cl.
CPC ........ *G06T 11/206* (2013.01); *G06F 19/3481* (2013.01); *G16H 40/63* (2018.01); *G05B 15/02* (2013.01)

(58) Field of Classification Search
CPC ......... A61B 6/542; A61B 6/487; A61B 6/545; A61B 6/0414; A61B 6/4233; A61B 6/481;
(Continued)

(56) References Cited

U.S. PATENT DOCUMENTS 4,739,480 A * 4/1988 Oono .................... G03B 42/047
250/584
6,795,526 B2 * 9/2004 Kump ...................... A61B 6/00
378/116

(Continued)

FOREIGN PATENT DOCUMENTS

JP  2009-268801 A  11/2009
JP  2014-014669 A  1/2014

OTHER PUBLICATIONS

Office Action dated Mar. 13, 2018, in Japanese Patent Application No. 2014-147041, filed Jul. 17, 2014, citing document No. AO, 23 pages.

*Primary Examiner* — Irakli Kiknadze
(74) *Attorney, Agent, or Firm* — Oblon, McClelland, Maier & Neustadt, L.L.P.

(57) ABSTRACT

An exposure management system according to an embodiment includes a processing circuitry. The processing circuitry is configured to calculate a deviation index related to a difference between a target exposure index indicating an index of an exposure value that is set as a target of an X-ray image taking process and an image-taking-period exposure index indicating an index of an exposure value observed during the X-ray image taking process. The processing circuitry is configured to control so as to cause a display device to display history information from a predetermined time period indicating at least one selected from between image-taking-period exposure indices and deviation indices.

11 Claims, 16 Drawing Sheets

(51) Int. Cl.
*G06F 19/00* (2018.01)
*G05B 15/02* (2006.01)

(58) Field of Classification Search
CPC ........... A61B 6/502; A61B 6/52; A61B 6/544;
A61B 6/547; A61B 6/566; A61B 6/583;
A61B 6/032; A61B 6/12; A61B 6/4417;
A61B 6/4441; A61B 6/4464; A61B
6/469; A61B 6/4494; B60J 1/2094; B65B
33/04; G05B 15/02; G06F 19/3406; G06F
19/3481; G06F 19/321; G06T 11/206;
G01T 1/026; G01T 1/2012; G01T 7/00;
G03B 42/047; G06K 2017/009; G06K
7/0008; G07C 9/00142
USPC .......................................... 378/4, 19, 62, 98
See application file for complete search history.

(56) References Cited

U.S. PATENT DOCUMENTS

| | | | |
|---|---|---|---|
| 2005/0209888 A1* | 9/2005 | Oowaki | A61B 6/542 |
| | | | 705/3 |
| 2011/0013742 A1* | 1/2011 | Zaiki | A61B 6/035 |
| | | | 378/15 |

* cited by examiner

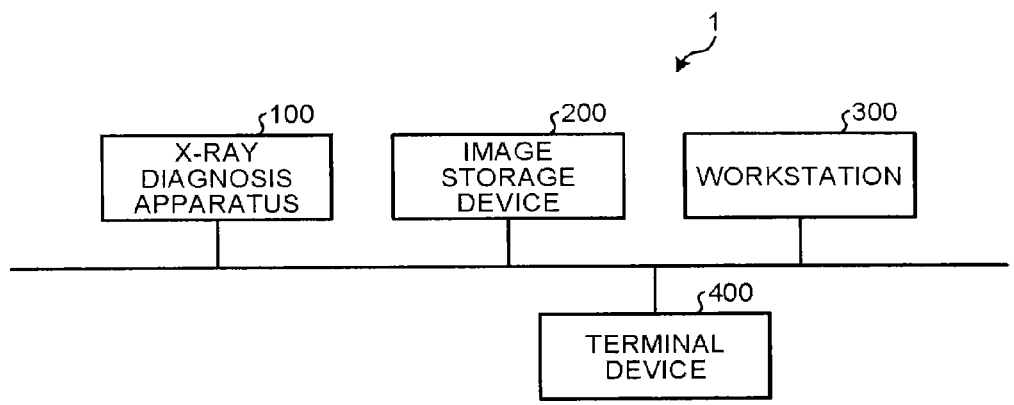
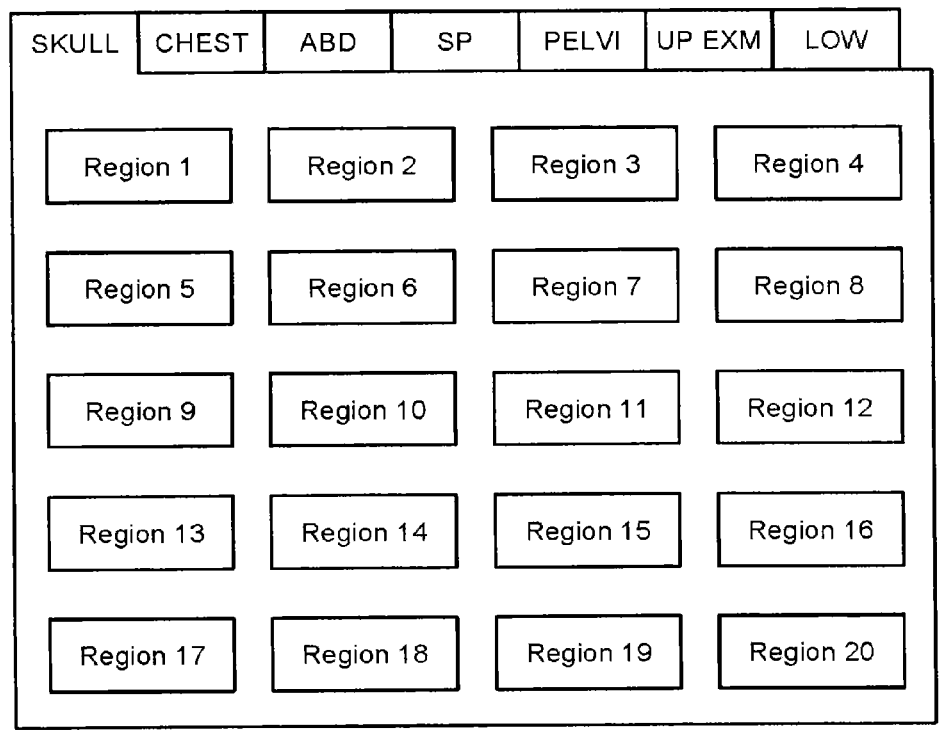

FIG.5
(A)
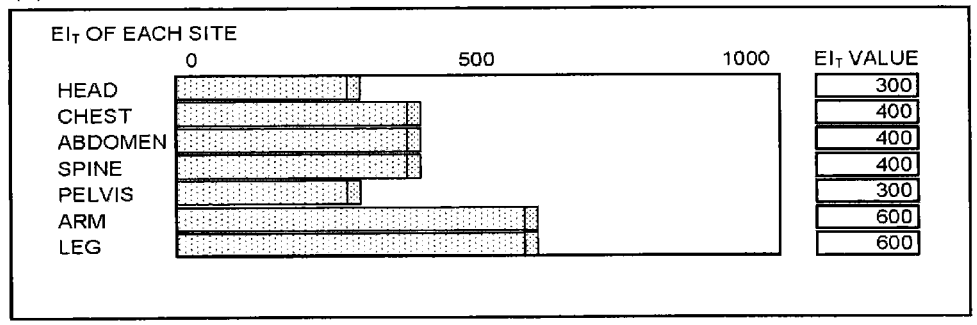
(B)
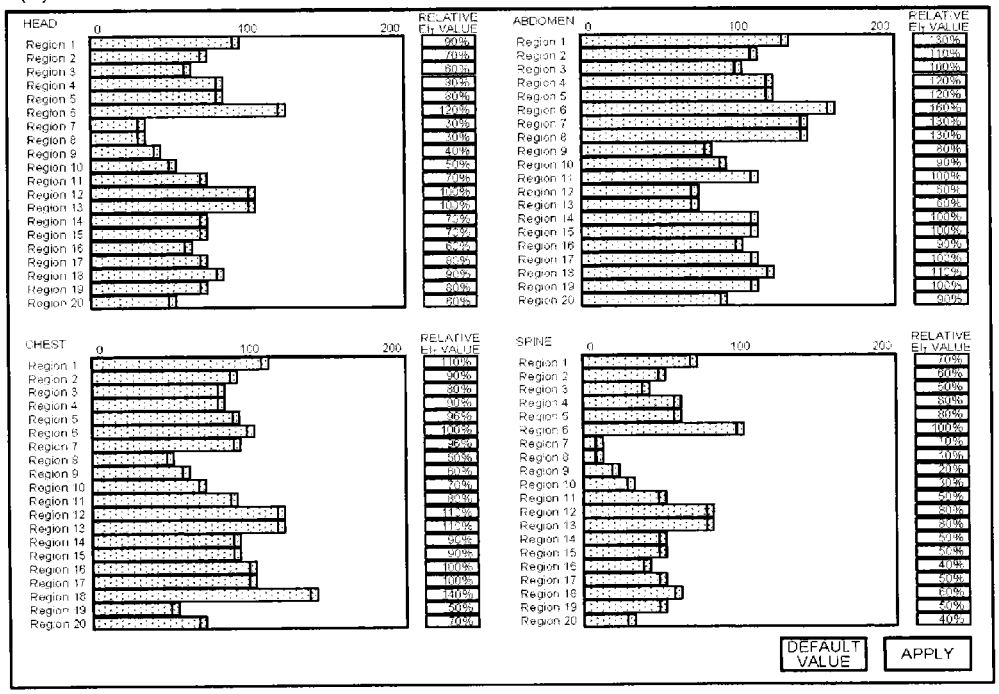

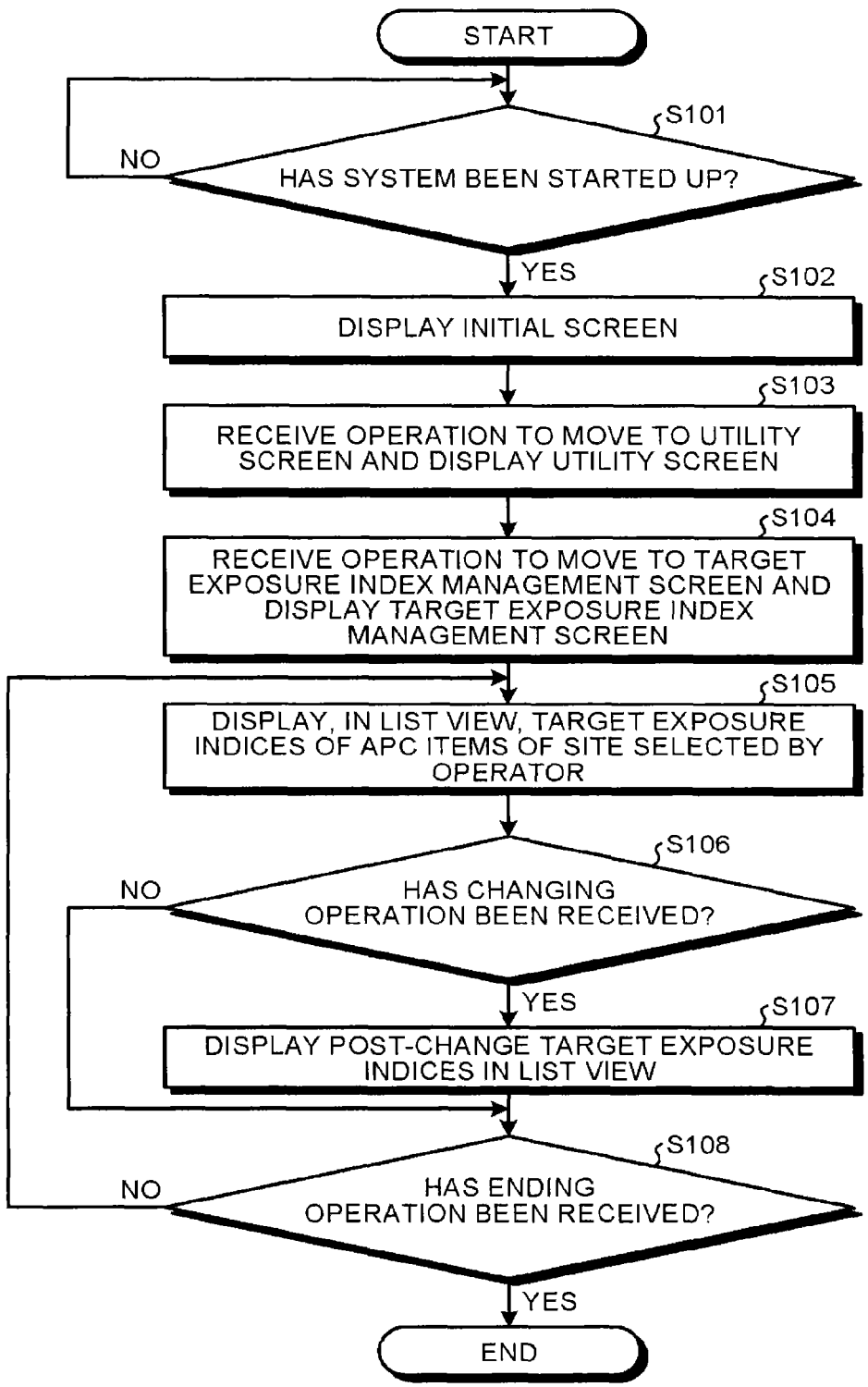

FIG.7A

LIST VIEW OF HISTORY OF DI'S

| TIME PERIOD | 2013/10/1 TO 2013/12/3 |
| --- | --- |
| PERSON WHO TOOK IMAGE | LABORATORY TECHNICIAN A |
| DETECTOR | FPD#001 |
| EXAMINATION ROOM | FIRST EXAMINATION ROOM |
| EXAMINED SITE | CHEST |
| | ALL |

| Description | Min | Max |
| --- | --- | --- |
| CHEST SIMPLE IMAGING: STANDING AND FRONT/BACK VIEW (UNSPECIFIED) | -5 | +5 |
| CHEST SIMPLE IMAGING: STANDING AND FRONT/BACK VIEW (A TO P) | -3 | +5 |
| CHEST SIMPLE IMAGING: STANDING AND FRONT/BACK VIEW (A TO P) TAKEN DURING INHALATION | -5 | +2 |
| CHEST SIMPLE IMAGING: STANDING AND FRONT/BACK VIEW (P TO A) | -3 | +3 |
| CHEST SIMPLE IMAGING: STANDING AND FRONT/BACK VIEW (P TO A) TAKEN DURING INHALATION | -5 | +5 |
| CHEST SIMPLE IMAGING: STANDING AND SIDE VIEW (R TO L) | -3 | +5 |
| CHEST SIMPLE IMAGING: STANDING AND SIDE VIEW (L TO R) | -5 | +2 |
| CHEST SIMPLE IMAGING: STANDING AND FIRST DIAGONAL POSITION (ANGLE UNSPECIFIED) | -3 | +3 |
| CHEST SIMPLE IMAGING: STANDING AND PULMONARY APEX VIEW | -5 | +5 |
| CHEST SIMPLE IMAGING: SUPINE AND FRONT/BACK VIEW (UNSPECIFIED) | -3 | +5 |

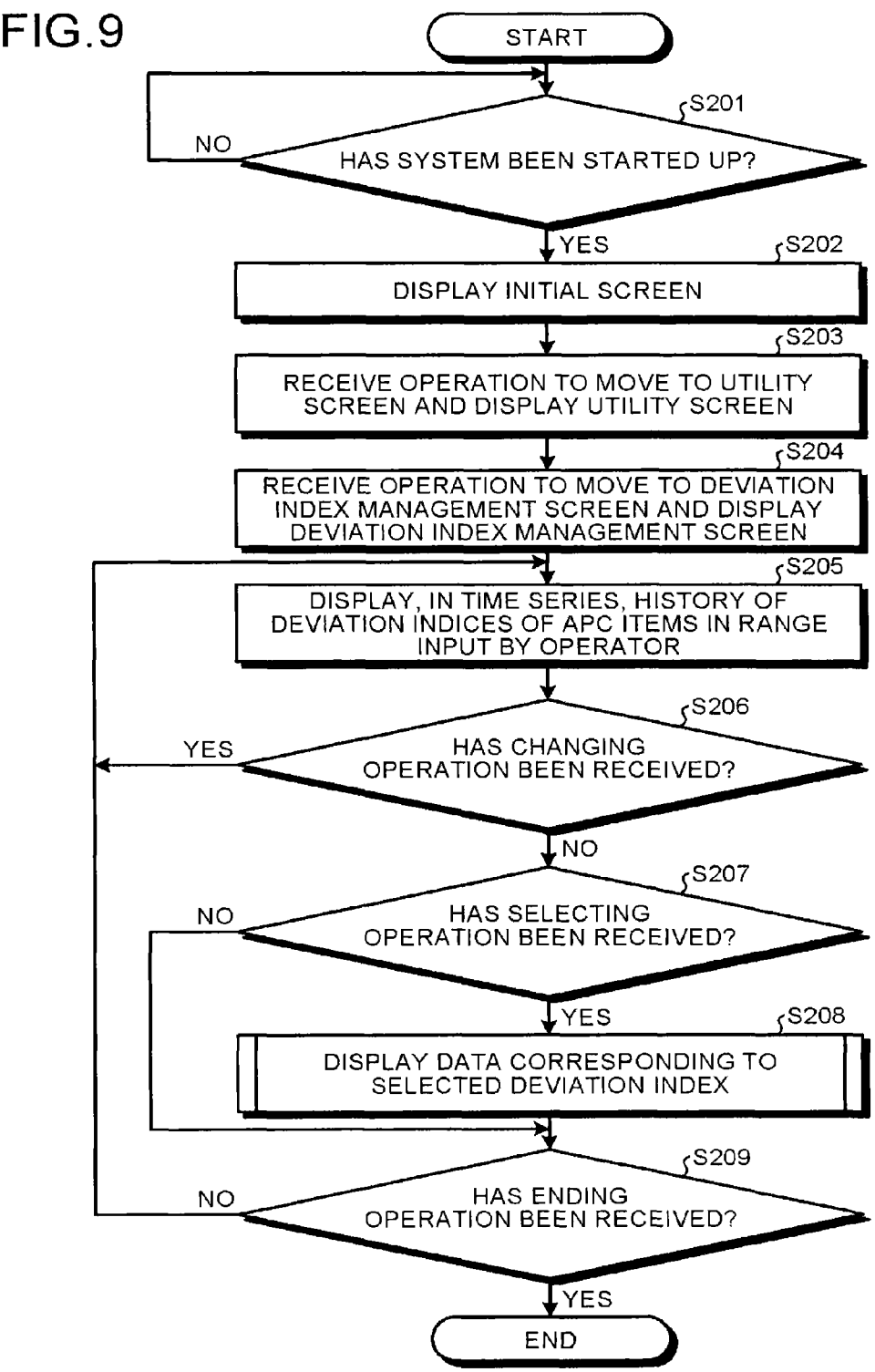

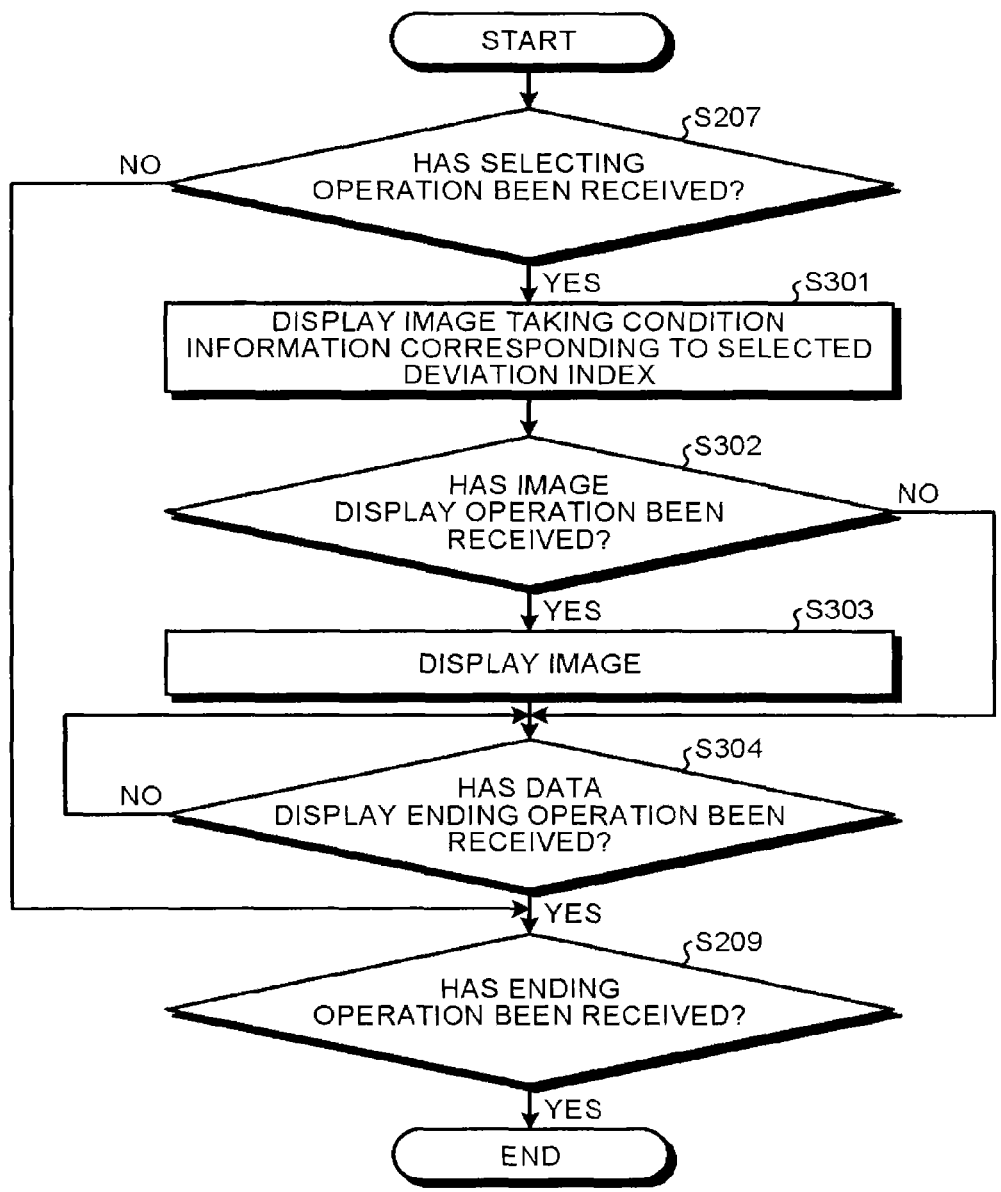

FIG.12

LIST OF CHANGE HISTORY OF TARGET EXPOSURE INDICES

| SITES | | INITIAL SETTING | CHANGE 1 | CHANGE 2 | CHANGE 3 | CHANGE 4 | CHANGE 5 |
|---|---|---|---|---|---|---|---|
| HEAD | Region 1 | 2013/1/2 | 2013/2/1 | 2013/3/10 | | | |
| | Region 2 | 2013/1/2 | | | | | |
| | Region 3 | 2013/1/2 | | | | | |
| | Region 4 | 2013/1/2 | | | | | |
| | Region 5 | 2013/1/2 | | | | | |
| | Region 6 | 2013/1/2 | | | | | |
| | Region 7 | 2013/1/2 | | | | | |
| | Region 8 | 2013/1/2 | | | | | |
| | Region 9 | 2013/1/2 | 2013/3/10 | 2013/4/1 | 2013/4/20 | | |
| | Region 10 | 2013/1/2 | | | | | |
| CHEST | Region 1 | 2013/1/2 | 2013/3/1 | | | | |
| | Region 2 | 2013/1/2 | | | | | |
| | Region 3 | 2013/1/2 | | | | | |
| | Region 4 | 2013/1/2 | 2013/3/1 | | | | |
| | Region 5 | 2013/1/2 | 2013/3/1 | | | | |
| | Region 6 | 2013/1/2 | | | | | |
| | Region 7 | 2013/1/2 | | | | | |
| | Region 8 | 2013/1/2 | | | | | |
| | Region 9 | 2013/1/2 | 2013/6/10 | | | | |
| | Region 10 | 2013/1/2 | | | | | |

NEXT ▷

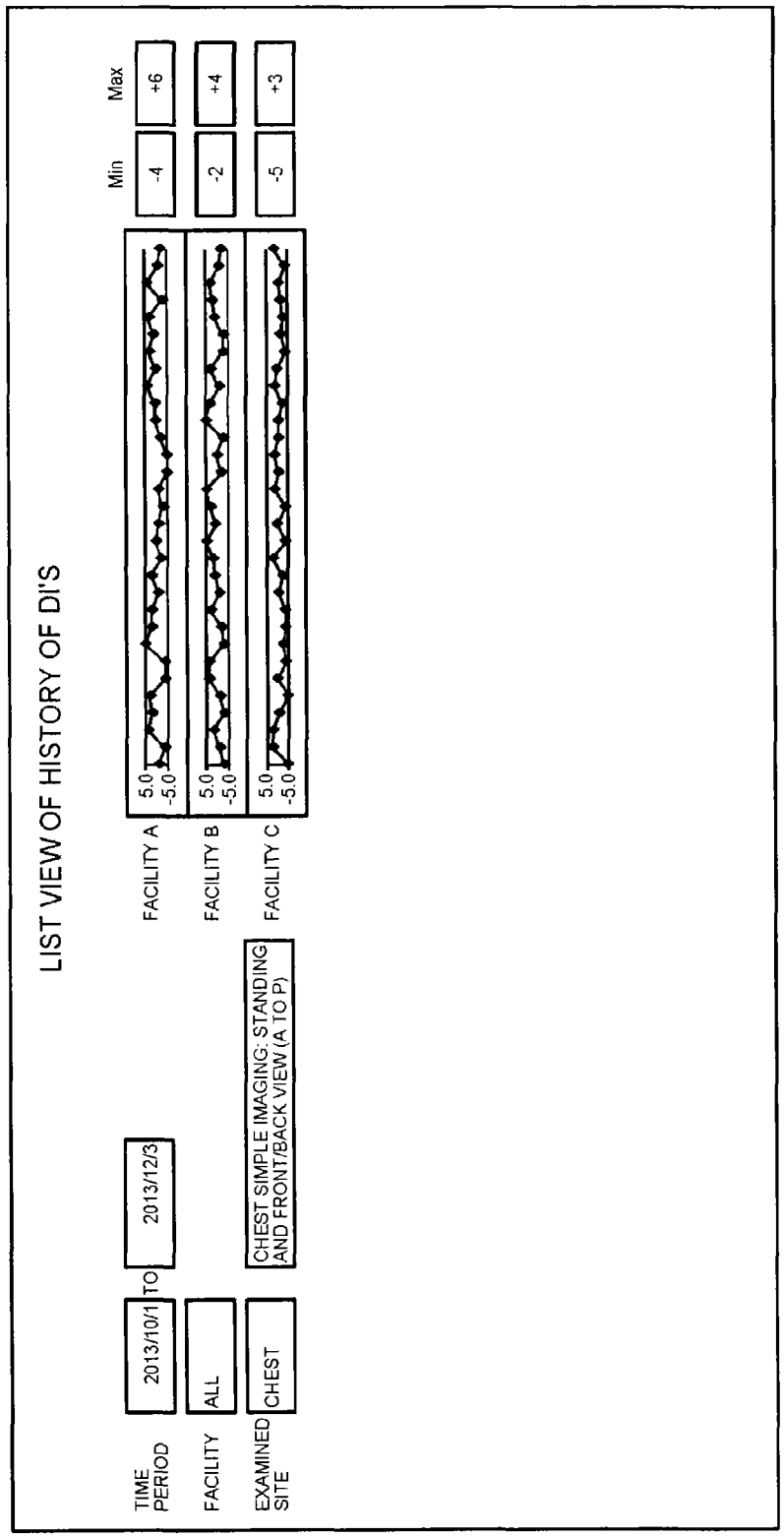

EXPOSURE MANAGEMENT SYSTEM

CROSS-REFERENCE TO RELATED APPLICATIONS

This application is based upon and claims the benefit of priority from Japanese Patent Application No. 2014-147041, filed on Jul. 17, 2014, the entire contents of all of which are incorporated herein by reference.

FIELD

Embodiments described herein relate generally to an exposure management system.

BACKGROUND

Conventionally, it is required that various types of information related to radiation amounts be displayed for the purpose of managing radiation exposure. For example, it is known that an Exposure Index (EI) and a Deviation Index (DI) are required to be displayed, which are defined as IEC 62494-1 by the International Electrotechnical Commission (IEC). In this situation, the exposure index is a value indicating an amount corresponding to an incident-to-detector radiation amount (D) calculated from a representative pixel value (V) of an image. The exposure index is a uniform index for radiation amounts that can be used even if systems from different manufacturers are being used. Further, the deviation index is an index value indicating how much difference is exhibited by an "EI" obtained for each image taking process, with respect to a "Target Exposure Index ($EI_T$)". The deviation index can be calculated by using an expression "DI=10 $\log_{10}(EI/EI_T)$". In this situation, "$EI_T$" is an intended "EI" value that is set for each medical examination.

While it is required that various types of information related to radiation amounts (hereinafter, "exposure") be displayed as noted above, examples of known techniques used for displaying an exposure index, a deviation index, and a target exposure index include a technique by which, for example, an exposure index and a deviation index are calculated every time an image taking process is performed, so that the exposure index and the deviation index that were calculated as well as a target exposure index are displayed as a result of the image taking process.

BRIEF DESCRIPTION OF THE DRAWINGS

FIG. 1 is a diagram for explaining an exemplary configuration of an exposure management system according to a first embodiment;

FIG. 2 is a drawing for explaining examined sites according to a conventional technique;

FIG. 5 is a drawing of examples of displaying target exposure indices according to the first embodiment;

FIG. 6 is a flowchart of a procedure in a process performed by the X-ray diagnosis apparatus according to the first embodiment;

FIG. 7A is a drawing of an example of displaying deviation indices according to a second embodiment;

FIG. 9 is a flowchart of a procedure in a process performed by an X-ray diagnosis apparatus according to the second embodiment;

FIG. 10 is another flowchart of the procedure in the process performed by the X-ray diagnosis apparatus according to the second embodiment;

FIG. 12 is a drawing of an example of a change history according to the third embodiment;

FIG. 14 is a drawing of an example of displaying deviation indices according to a fourth embodiment; and

DETAILED DESCRIPTION

Figure 3:
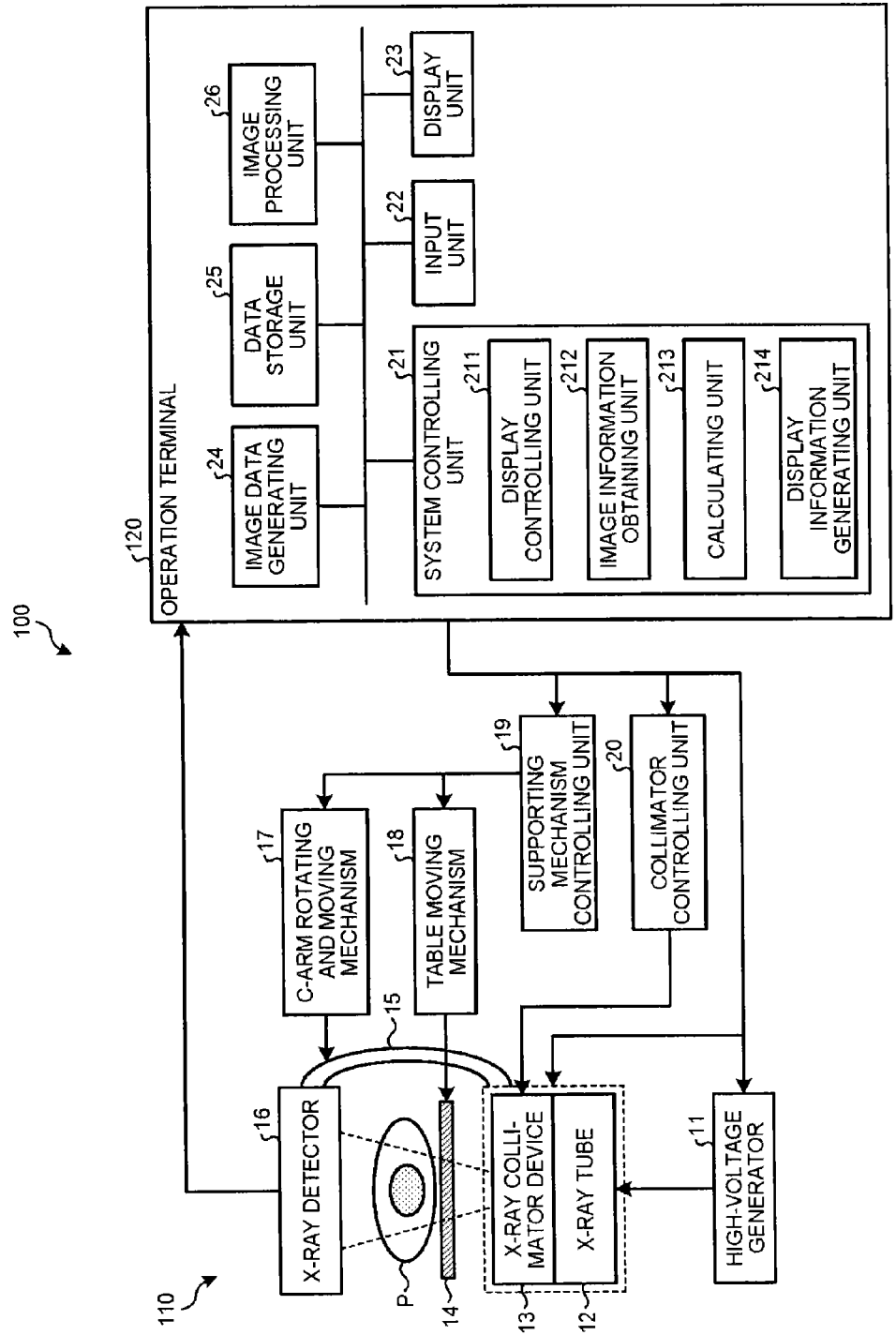
FIG. 3 is a diagram of an exemplary configuration of an X-ray diagnosis apparatus according to the first embodiment.

According to an embodiment, an exposure management system according to an embodiment includes a processing circuitry. The processing circuitry is configured to calculate a deviation index related to a difference between a target exposure index indicating an index of an exposure value that is set as a target of an X-ray image taking process and an image-taking-period exposure index indicating an index of an exposure value observed during the X-ray image taking process. The processing circuitry is configured to control so as to cause a display device to display history information from a predetermined time period indicating at least one selected from between image-taking-period exposure indices and deviation indices.

Exemplary embodiments of an exposure management system will be explained in detail below, with reference to the accompanying drawings. In the following sections, examples will be explained in which processes performed in the exposure management system are performed by an X-ray diagnosis apparatus; however, the processes explained in the exemplary embodiments may be performed by any apparatus or device in the exposure management system.

First Embodiment

First, an exemplary configuration of an image display system according to a first embodiment will be explained. FIG. 1 is a diagram for explaining an exemplary configuration of an exposure management system 1 according to the first embodiment. As illustrated in FIG. 1, the exposure management system 1 according to the first embodiment includes an X-ray diagnosis apparatus 100, an image storage device 200, a workstation 300, and a terminal device 400. The apparatus and the devices illustrated in FIG. 1 are capable of either directly or indirectly communicating with one another via, for example, an intra-hospital Local Area Network (LAN) provided in a hospital. For example, if a Picture Archiving and Communication System (PACS) has been introduced into the exposure management system 1, the apparatus and the devices transmit and receive X-ray images and the like to and from one another according to a Digital Imaging and Communications in Medicine (DICOM) standard.

The image storage device 200 is a database configured to store medical images therein. For example, the image storage device 200 puts image data transmitted thereto from the X-ray diagnosis apparatus 100 into a storage unit and stores the image data therein. In this situation, the image data stored in the image storage device 200 is stored while being kept in correspondence with subject IDs, medical examination IDs, apparatus IDs, series IDs, and the like. With this arrangement, the workstation 300 and the terminal device 400 are able to obtain necessary image data from the image storage device 200, by conducting a search with the use of a subject ID, a medical examination ID, an apparatus ID, a series ID, or the like.

The workstation 300 is an image processing device configured to perform an image processing process on a medical image. More specifically, the workstation 300 generates a display image by performing any of various types of image processing processes on the image data obtained from the X-ray diagnosis apparatus 100 or the image storage device 200. Further, the workstation 300 transmits the generated display image to the image storage device 200. When transmitting the display image to the image storage device 200, the workstation 300 transmits, for example, the subject ID, the medical examination ID, the apparatus ID, the series ID, and the like, as additional information.

The terminal device 400 is a device used for enabling medical doctors and laboratory technicians working in the hospital to view the medical image. For example, the terminal device 400 may be a Personal Computer (PC), a tablet-style PC, a Personal Digital Assistant (FDA), a portable phone, or the like operated by the medical doctors and the laboratory technicians working in the hospital. More specifically, the terminal device 400 is configured to obtain the display image from the image storage device 200 and to cause a display monitor to display the obtained display image. As a result, any of the doctors and the laboratory technicians who is the viewer is able to view the display image.

The X-ray diagnosis apparatus 100 is configured to generate an X-ray image by radiating X-rays onto an examined subject and detecting X-rays that have passed through the subject. In this situation, in relation to the X-ray diagnosis apparatus 100, it is important to manage not only radiation exposure in units of subjects, but also radiation exposure in units of apparatuses, in units of examination rooms, and also, in units of facilities. Accordingly, it is stipulated that an Exposure Index (EI) and a Deviation Index (DI) compliant with IEC 62494-1 as described above are required to be displayed.

However, conventional X-ray diagnosis apparatuses are configured to set a target exposure index for each examined site and to only display an exposure index and a deviation index after an image taking process. Consequently, it requires a lot of labor to manage radiation exposure in units of apparatuses, in units of examination rooms, and in units of facilities. For example, an X-ray diagnosis apparatus is configured to define examined sites in "broader categories" and examined site in "narrower categories" in order to facilitate setting of image taking parameters, so that when an operator selects a specific examined site in a "broader category" from a plurality of examined sites in the "broader categories", a plurality of examined sites in "narrower categories" are displayed. When the operator further selects a specific examined site in a "narrower category" from among the displayed examined sites in the "narrower categories", the X-ray diagnosis apparatus is automatically set with image taking parameters (e.g., an X-ray condition, an examination method, a detector size, a distance between an X-ray focal point and the detector, a distance between the subject and the detector, a target exposure index, a display condition, an output condition, and/or the like) that correspond to the selected examined site.

Currently, X-ray diagnosis apparatuses usually have twenty or more examined sites in the "narrower categories" that are included in each of the examined sites in the "broader categories" and twenty or more image taking parameters that need to be set for each of the examined sites in the "narrower categories". Thus, the labor of the operator is significantly reduced by the automatic setting mechanism described above. Further, because there are a large number of image taking parameters that need to be set for each of the examined sites in the "narrower categories", one screen is used for making the settings for each of the examined sites in the "narrower categories". With these arrangements, it is possible to make the settings in advance while checking all the parameters of a single examined site in a "narrower category" on the one parameter setting screen.

FIG. 2 is a drawing for explaining examined sites according to a conventional technique. FIG. 2 illustrates an example of a selection screen used for selecting an examined site, when setting the image taking parameters. For example, with a conventional X-ray diagnosis apparatus, as illustrated in FIG. 2, an examined site in a "broader category" is selected by selecting one of the tabs shown as "SKULL", "CHEST", "ABD", "SP", "PELVI", "UP EXM", "LOW", and the like. In this situation, for example, when the "SKULL" tab is selected as illustrated in FIG. 2, examined sites in the "narrower categories" such as "Region 1" to "Region 20" are displayed under the tab.

The operator selects a desired examined site from among the regions "Region 1" to "Region 20" being displayed. For example, when the operator selects the "Region 1" being displayed, a parameter setting screen that corresponds to "Region 1" will be displayed. The parameter setting screen includes areas for setting all the image taking parameters related to "Region 1", and the image taking parameters also include a target exposure index.

As explained above, the target exposure index is set for each of the examined sites in the "narrower categories". Accordingly, when an operator is to set target exposure indices by using the selection screen illustrated in FIG. 2, the operator first selects an examined site in a "broader category" by selecting a tab, and further selects examined sites in the "narrower categories", one after another, from among the plurality of examined sites in the "narrower categories" included under the tab, so as to have a corresponding parameter setting screen displayed every time so that the operator is able to set each of the target exposure indices. After that, when the target exposure index has been set for each of all the examined sites in the "narrower categories" included under the single tab, another tab is selected so as to make the settings in a similar manner.

Accordingly, when only the parameter setting screens are provided in which the target exposure indices are set together with the other image taking parameters as described above, it is difficult to check to see whether the setting value set for each of the examined sites satisfies an exposure management policy of the entire facility. Thus, even if the target exposure indices are being used, the target exposure indices are not sufficiently utilized in the exposure management of all the image taking processes. Further, when the target exposure index, the exposure index, and the deviation index are simply displayed on the screen after each image taking process, it is not possible to obtain statistical information about deviation indices of image taking processes that have been performed in a facility or in an examination room. Consequently, even if there are one or more too large deviation indices or even if deviation indices are not uniform, it is not possible to obtain information that would be useful for improving the situation.

Further, because an initial value of the target exposure index is determined on the basis of a result of an image taking process performed on a phantom or the like, prior to the shipment of each X-ray diagnosis apparatus from the manufacturer, for example, when an image taking process is performed on an actual human body after the X-ray diagnosis apparatus is installed, the deviation index may exhibit a divergence from zero in some situations. In those situations, if an image taking process is performed with a setting that makes the deviation index closer to zero, the radiation exposure amount of the subject may become too large, or the image quality may become lower than expected because of too small a radiation amount. In those situations, it is necessary to reset the target exposure index; however, it is not easy to determine the value to which the target exposure index should be reset. Further, because the changing of the target exposure index is related to radiation exposure of the subject, it is necessary that an administrator who manages the X-ray diagnosis apparatus or the facility changes the target exposure index with an intention. It is also necessary to ensure that a history of changes is available at a later time.

To cope with this situation, the X-ray diagnosis apparatus 100 according to the first embodiment makes it possible to efficiently manage radiation exposure by using a configuration described in detail below. More specifically, the X-ray diagnosis apparatus 100 makes it possible to efficiently manage the radiation exposure by making it possible to manage target exposure indices, deviation indices, and exposure indices for the entire system.

FIG. 3 is a diagram of an exemplary configuration of the X-ray diagnosis apparatus 100 according to the first embodiment. As illustrated in FIG. 3, the X-ray diagnosis apparatus 100 according to the first embodiment includes an apparatus main body 110 and an operation terminal 120. As illustrated in FIG. 3, the apparatus main body 110 includes a high-voltage generator 11, an X-ray tube 12, an X-ray collimator device 13, a table 14, a C-arm 15, an X-ray detector 16, a C-arm rotating and moving mechanism 17, a table moving mechanism 18, a supporting mechanism controlling unit 19, and a collimator controlling unit 20. As illustrated in FIG. 3, the operation terminal 120 includes a system controlling unit 21, an input unit 22, a display unit 23, an image data generating unit 24, a data storage unit 25, and an image processing unit 26.

The functions of the above-described respective units are configured as programs and are implemented in a way that circuitry executes the programs. For example, the processing functions respectively implemented by the supporting mechanism controlling unit 19, the collimator controlling unit 20, the system controlling unit 21, the image data generating unit 24, and the image processing unit 26 are stored in a form of computer-executable programs and stored in the data storage unit 25 (also referred to as an "data storage circuitry"). The circuitry loads the programs from the data storage unit 25 and executes the programs, thereby implementing the functions corresponding to the respective programs.

A single circuitry or multiple circuitry may implement the functions. In other words, a single circuitry may load the programs corresponding to the respective functions and implement the corresponding functions, or multiple circuitry may load the programs corresponding to the functions different from one another and implement the corresponding respective functions. The above-described circuitry are processors that implement the functions corresponding to the respective programs in a way that the circuitry loads the programs from the data storage unit 25 and execute the programs.

The term "processor" used in the above description means, for example, a central preprocess unit (CPU) and a graphics processing unit (GPU), or a circuit such as an application specific integrated circuit (ASIC), a programmable logic device (for example, a simple programmable logic device (SPLD)), a complex programmable logic device (CPLD), and a field programmable gate array (FPGA). The processor implements a function by loading and executing a program stored in a storage circuit. Instead of being stored in a storage circuit, the program may be built directly in a circuit of the processor. In this case, the processor implements a function by loading and executing the program built in the circuit. The processors in the embodiment are not limited to a case in which each of the processors is configured as a single circuit. Multiple separate circuits may be combined to be configured as one processor that implements the respective functions.

The high-voltage generator 11 is configured, under control of the system controlling unit 21, to generate a high voltage and to supply the generated high voltage to the X-ray tube 12. The X-ray tube 12 is configured to generate X-rays by using the high voltage supplied from the high-voltage generator 11.

The X-ray collimator device 13 is configured, under control of the collimator controlling unit 20, to converge the X-rays generated by the X-ray tube 12 so that the X-rays are selectively radiated onto a region of interest of a subject P. For example, the X-ray collimator device 13 includes four slidable collimator vanes. By sliding the collimator vanes under the control of the collimator controlling unit 20, the X-ray collimator device 13 causes the X-rays generated by the X-ray tube 12 to be converged and radiated onto the subject P. The X-ray tube 12 and the X-ray collimator device 13 may collectively be referred to as an X-ray tube device. The table 14 is a bed on which the subject P is placed and is positioned on a couch (not illustrated). The subject P is not included in the apparatus main body 110.

The X-ray detector 16 is configured to detect X-rays that have passed through the subject P. For example, the X-ray detector 16 includes detecting elements that are arranged in a matrix formation. Each of the detecting elements is configured to convert the X-rays that have passed through the subject P into an electrical signal, to accumulate the electrical signals therein, and to transmit the accumulated electrical signals to the image data generating unit 24.

The C-arm 15 is configured to hold the X-ray tube 12, the X-ray collimator device 13, and the X-ray detector 16. The X-ray tube 12 with the X-ray collimator device 13 and the X-ray detector 16 are positioned by the C-arm 15 so as to oppose each other while the subject P is interposed therebetween.

The C-arm rotating and moving mechanism 17 is a mechanism configured to rotate and move the C-arm 15. The table moving mechanism 18 is a mechanism configured to move the table 14. The supporting mechanism controlling unit 19 is configured, under the control of the system controlling unit 21, to adjust the rotation and the moving of the C-arm 15 and the moving of the table 14, by controlling the C-arm rotating and moving mechanism 17 and the table moving mechanism 18. The supporting mechanism controlling unit 19 is also referred to as a supporting mechanism control circuitry that loads the program corresponding to the above-described supporting mechanism controlling function from the data storage unit 25 and executes the program. The collimator controlling unit 20 is configured, under the control of the system controlling unit 21, to control the radiation range of the X-rays radiated onto the subject P, by adjusting the opening degree of the collimator vanes included in the X-ray collimator device 13. The collimator controlling unit 20 is also referred to as a collimator controlling circuitry that loads the program corresponding to the above-described collimator controlling function from the data storage unit 25 and executes the program.

The image data generating unit 24 is configured to generate image data by using the electrical signals converted from the X-rays by the X-ray detector 16 and to store the generated image data into the data storage unit 25. For example, the image data generating unit 24 generates the image data by performing a current/voltage converting process, an Analog/Digital (A/D) converting process, and/or a parallel/serial converting process, on the electrical signals received from the X-ray detector 16.

Further, the image data generating unit 24 generates an X-ray image from the generated image data and stores the generated X-ray image into the data storage unit 25. The image data generating unit 24 is also referred to as an image data generating circuitry that loads the program corresponding to the above-described image data generating function from the data storage unit 25 and executes the program.

The data storage unit 25 is configured to store therein the image data generated by the image data generating unit 24. Further, the data storage unit 25 is configured to store therein a target exposure index that has been set for each examined site. The data storage unit 25 is also referred to as an data storage circuitry that stores the programs corresponding to the respective functions.

The image processing unit 26 is configured to perform any of various types of image processing processes on the image data stored in the data storage unit 25. For example, by processing a plurality of X-ray images that are in a time series and are stored in the data storage unit 25, the image processing unit 26 generates a moving picture. The image processing unit 26 is also referred to as an image processing circuitry that loads the program corresponding to the above-described image processing function from the data storage unit 25 and executes the program.

The input unit 22 is configured to receive various types of instructions from an operator. For example, the input unit 22 includes a mouse, a keyboard, a button, a trackball, a joystick, and/or the like. The input unit 22 is configured to transfer the instructions received from the operator to the system controlling unit 21. For example, the input unit 22 receives various types of instructions related to the exposure management and transfers the received instructions to the system controlling unit 21. The input unit 22 is also referred to as an input circuitry.

The display unit 23 is configured to display a Graphical User Interface (GUI) used for receiving instructions from the operator, the image data stored in the data storage unit 25, and the like. For example, the display unit 23 displays various types of information related to the exposure management. The display unit 23 is also referred to as a display.

The system controlling unit 21 is configured to control operations of the entirety of the X-ray diagnosis apparatus 100. For example, the system controlling unit 21 controls the amount of X-rays radiated onto the subject and turns on and off the X-ray radiation, by controlling the high-voltage generator 11 and adjusting the voltage applied to the X-ray tube 12, according to instructions from the operator transferred thereto from the input unit 22. Further, for example, the system controlling unit 21 controls the supporting mechanism controlling unit 19 and adjusts the rotation and the moving of the C-arm 15 and the moving of the table 14, according to instructions from the operator. Further, for example, the system controlling unit 21 controls the radiation range of the X-rays radiated onto the subject, by controlling the collimator controlling unit 20 and adjusting the opening degree of the collimator vanes included in the X-ray collimator device 13, according to instructions from the operator. Further, the system controlling unit 21 controls the image data generating process performed by the image data generating unit 24 and the image processing processes performed by the image processing unit 26, as well as analyzing processes, according to instructions from the operator. Furthermore, the system controlling unit 21 communicates with the image storage device 200 and the workstation 300 so as to transmit the X-ray image taken by the apparatus main body 110 thereto. The system controlling unit 21 is also referred to as a system controlling circuitry that loads the program corresponding to the above-described system controlling function from the data storage unit 25 and executes the program.

In this situation, as illustrated in FIG. 3, the system controlling unit 21 includes a display controlling unit 211, an image information obtaining unit 212, a calculating unit 213, and a display information generating unit 214. In other words, the system controlling circuitry that implements the system controlling function performs the processing, which will be described below, by loading the programs corresponding to the functions of the display controlling unit 211, the image information obtaining unit 212, the calculating unit 213, and the display information generating unit 214 from the data storage unit 25 and executing the programs.

The display controlling unit 211 is configured to exercise control so as to cause a display device in the display unit 23 to display the GUI used for receiving instructions from the operator and any of the images stored in the data storage unit 25. Further, the display controlling unit 211 is configured to exercise control so as to cause the display unit 23 to display display information generated by the display information generating unit 214 (explained later). Details of the display information generated by the display information generating unit 214 will be explained later.

The image information obtaining unit 212 is configured to obtain information used for calculating an Exposure Index (EI). More specifically, the image information obtaining unit 212 obtains information about a representative pixel value of the X-ray image detected by the X-ray detector 16. The calculating unit 213 is configured to calculate the exposure index by using a conversion table that is stored therein in advance and is used for converting a pixel value into an exposure value, on the basis of the information about the representative pixel value obtained by the image information obtaining unit 212. Further, the calculating unit 213 is configured to calculate a Deviation Index (DI) from a Target Exposure Index ($EI_T$) that is set in advance and the calculated exposure index. For example, the calculating unit 213 calculates the deviation index expressed as "$DI = 10 \log_{10}(EI/EI_T)$". The display information generating unit 214 is configured to generate various types of display information to be displayed under the control of the display controlling unit 211. More specifically, the display information generating unit 214 is configured to generate display information including the target exposure index, the exposure index, and the deviation index.

In this situation, the X-ray diagnosis apparatus 100 according to the first embodiment makes it possible to efficiently manage radiation exposure, by realizing a display of target exposure indices that are easy to see and easy to set, with respect to information about a plurality of examined sites. In that situation, the display information generating unit 214 generates the display information including the target exposure indices for image taking items of the plurality of examined sites. After that, the display controlling unit 211 causes the display unit 23 to display the generated display information. In other words, the display controlling unit 211 causes the display unit to display, in a list view, the information about the target exposure index that is set for each of the image taking items of the examined sites of which X-ray images are taken.

Figure 4:
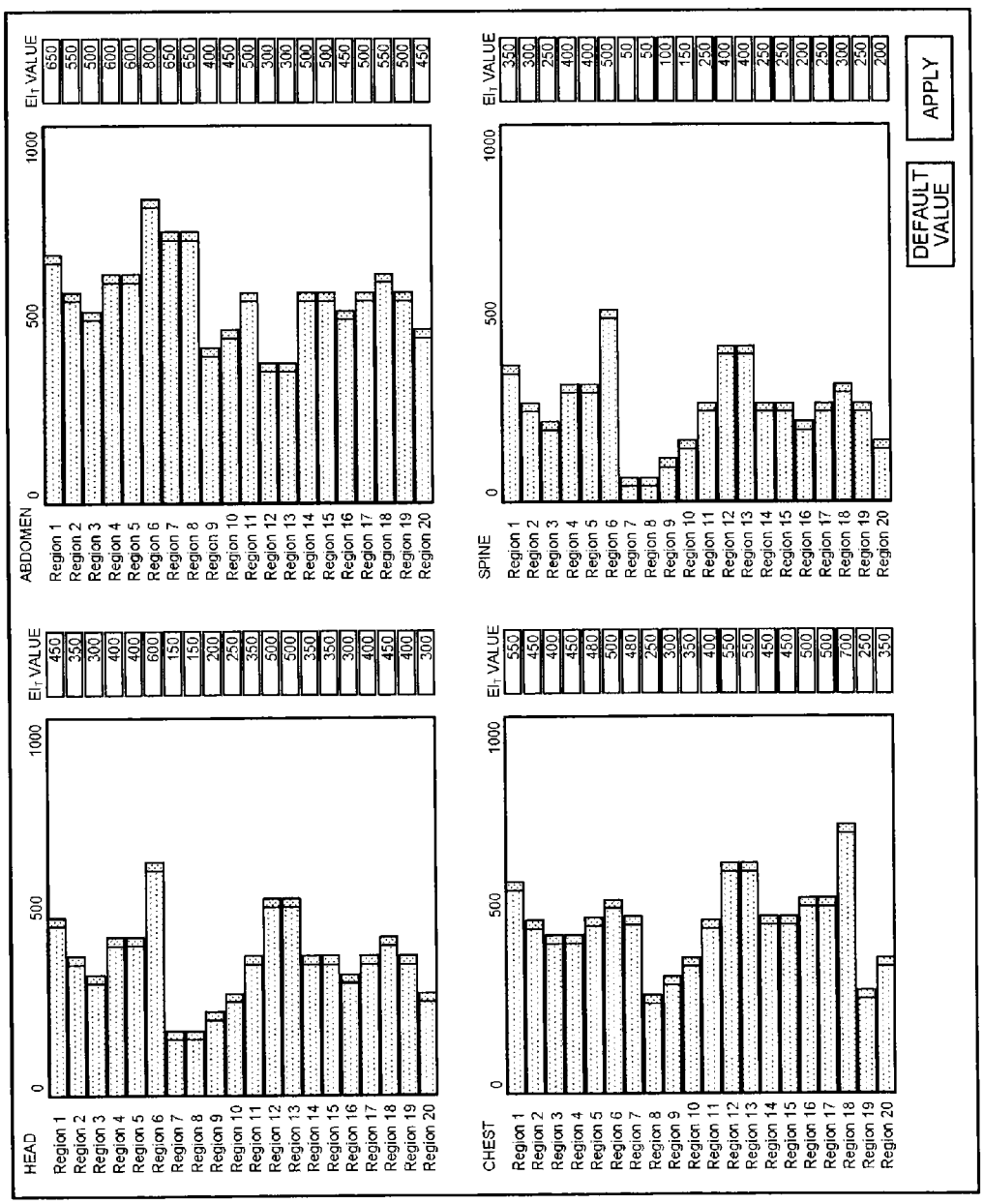
FIG. 4 is a drawing of an example of displaying target exposure indices according to the first embodiment.

In this situation, the examined sites in the first embodiment include less detailed categories of sites of the human body called "examined sites in the 'broader categories'" such as the head, the chest, the abdomen, the pelvis, the lumbar vertebrae, and the like and more detailed categories called "examined sites in the 'narrower categories'" including image taking methods. The "examined sites in the 'narrower categories'" may include, for example, "chest simple imaging: standing and front/back view, (Anterior to Posterior [A to P])", "chest simple imaging: standing and front/back view (A to P) taken during inhalation", "chest simple imaging: standing and front/back view (P to A)", and "chest simple imaging: standing and front/back view (P to A) taken during inhalation". In the following sections, the "examined sites in the 'narrower categories'" may be referred to as APC items. Next, examples of displaying the target exposure indices according to the first embodiment will be explained, with reference to FIGS. 4 and 5. FIGS. 4 and 5 are drawings of the examples of displaying the target exposure indices according to the first embodiment.

For example, as illustrated in FIG. 4, the display controlling unit 211 displays, in a list view, charts and absolute values of target exposure indices called "$EI_T$ values" for the examined sites in the narrower categories indicated as "Region 1" to "Region 20" that are included in each of the examined sites in the broader categories indicated as the "head", the "chest", the "abdomen", and the "spine". In other words, the display information generating unit 214 reads the target exposure indices for the examined sites in the "narrower categories" from the data storage unit 25, generates the display information including the charts and the absolute values of the target exposure indices that are grouped together in correspondence with the examined sites in the broader categories, and sends the generated display information to the display controlling unit 211, so that the display information is displayed by the display unit 23.

As illustrated in FIG. 4, because the chart is displayed to indicate the target exposure indices of the examined sites in the narrower categories for each of the examined sites in the broader categories, it is possible to intuitively understand the differences among the target exposure indices for each single site in the broader categories. Further, it is possible to arbitrarily set the target exposure indices illustrated in FIG. 4, via the input unit 22. For example, by performing an operation on any of the chart bars corresponding to the "regions" representing the examined sites in the narrower categories while using a pointing device such as the mouse, it is possible to arbitrarily change the target exposure index for each of the examined sites in the narrower categories. Further, it is also possible to arbitrarily change any of the target exposure indices indicated with the absolute values, by using an input device such as the keyboard. In this situation, when any of the target exposure indices has been changed, the post-change target exposure index is stored into the data storage unit 25. The display illustrated in FIG. 4 is merely an example. It is acceptable to arbitrarily change the layout of the information and the like.

FIG. 4 illustrates the example in which the target exposure indices for the examined sites in the narrower categories are indicated by using the absolute values. However, possible embodiments are not limited to this example. For instance, it is also acceptable to indicate the target exposure indices by using relative values. For example, as illustrated in FIG. 5 (A), the display controlling unit 211 may cause the absolute value of a target exposure index to be displayed as a reference, for each of the examined sites in the broader categories. Further, as illustrated in FIG. 5 (B), the display controlling unit 211 may cause information to be displayed in which a target exposure index for each of the examined sites in the narrower categories is indicated as a relative percentage with respect to the reference target exposure index expressed with the absolute value, for each of the examined sites in the broader categories.

For example, the display information generating unit 214 generates the information illustrated in FIG. 5(B) by calculating the percentage of the target exposure index set for each of the examined sites in the narrower categories, with respect to the target exposure index set as the reference value for each of the broader categories and further sends the generated information to the display controlling unit 211, so that the generated information is displayed by the display unit 23. In this situation, it is possible to arbitrarily set the target exposure indices illustrated in FIG. 5, via the input unit 22. As noted above, the X-ray diagnosis apparatus according to the first embodiment makes it possible to efficiently manage the radiation exposure, by realizing the list-view display of the target exposure indices set for the examined sites in the narrower categories and receiving the changing operation to change any of the values.

Next, a process performed by the X-ray diagnosis apparatus 100 according to the first embodiment will be explained, with reference to FIG. 6. FIG. 6 is a flowchart of a procedure in the process performed by the X-ray diagnosis apparatus 100 according to the first embodiment. As illustrated in FIG. 6, in the X-ray diagnosis apparatus 100 according to the first embodiment, for example, when the system is started up (step S101: Yes), the display controlling unit 211 displays an initial screen (step S102). After that, the display controlling unit 211 receives an operation to move to a utility screen via the input unit 22 and thus displays the utility screen (step S103).

In this situation, by inputting a user ID and a password or the like when performing the operation to move to the utility screen, the operator is authorized that he/she is an operator who is allowed to change any of the target exposure indices. Subsequently, the display controlling unit 211 receives an operation to move from the utility screen to a target exposure index management screen via the input unit 22 and thus causes the display unit 23 to display the target exposure index management screen (step S104). After that, the display controlling unit 211 causes target exposure indices for the APC items of a site selected by the operator to be displayed in a list view (step S105).

Subsequently, when having received a changing operation to change any of the target exposure indices (step S106: Yes), the display information generating unit 214 generates post-change display information, so that the display controlling unit 211 causes the generated display information (target exposure indices) to be displayed in a list view (step S107). Subsequently, the display controlling unit 211 judges whether or not an ending operation has been received (step S108). In this situation, if no ending operation has been received (step S108: No), the process returns to step S105 so that the display controlling unit 211 continues to display the list-view display. On the contrary, if an ending operation has been received (step S108: Yes), the X-ray diagnosis apparatus 100 ends the process.

As explained above, according to the first embodiment, the display controlling unit 211 causes the display unit 23 to display, in the list view, the information about the target exposure indices set for the image taking items of the examined sites of which the X-ray images are taken. Consequently, the X-ray diagnosis apparatus 100 according to the first embodiment makes it possible to check the plurality of target exposure indices at the same time and to efficiently manage the radiation exposure in units of apparatuses, in units of examination rooms, and in units of facilities.

Further, according to the first embodiment, the display controlling unit 211 causes one or both of the absolute values and the relative values of the target exposure indices to be displayed in the list view, as the information about the target exposure indices. Consequently, the X-ray diagnosis apparatus 100 according to the first embodiment makes it possible to realize the display by switching between the pieces of information to make it easier for the operator to make a comparison.

Further, according to the first embodiment, the input unit 22 receives the changing operation to change any of the target exposure indices. Consequently, the X-ray diagnosis apparatus 100 according to the first embodiment makes it possible to set the target exposure indices while looking at the list view of the target exposure indices.

Second Embodiment

In the first embodiment, the example is explained in which the target exposure indices are displayed in the list view in such a manner that each of the target exposure indices can be set individually. In a second embodiment, an example will be explained in which history information of deviation indices during a predetermined time period is displayed. The second embodiment is different from the first embodiment for the contents of the processes performed by the display controlling unit 211 and the display information generating unit 214. In the following sections, the second embodiment will be explained while a focus is placed on the differences.

The display controlling unit 211 according to the second embodiment is configured to exercise control so as to cause the display unit 23 to display the history information of the deviation indices during the predetermined time period. More specifically, the display controlling unit 211 exercises control so as to cause the display unit 23 to display a history of deviation indices exhibited under each image taking condition during the predetermined time period. In this situation, the display controlling unit 211 uses at least one selected from among the operator, the detector, the examination room, and the examined site, as the image taking condition. The display information generating unit 214 according to the second embodiment is configured to generate the history information of the deviation indices during the predetermined time period.

Figure 7B:
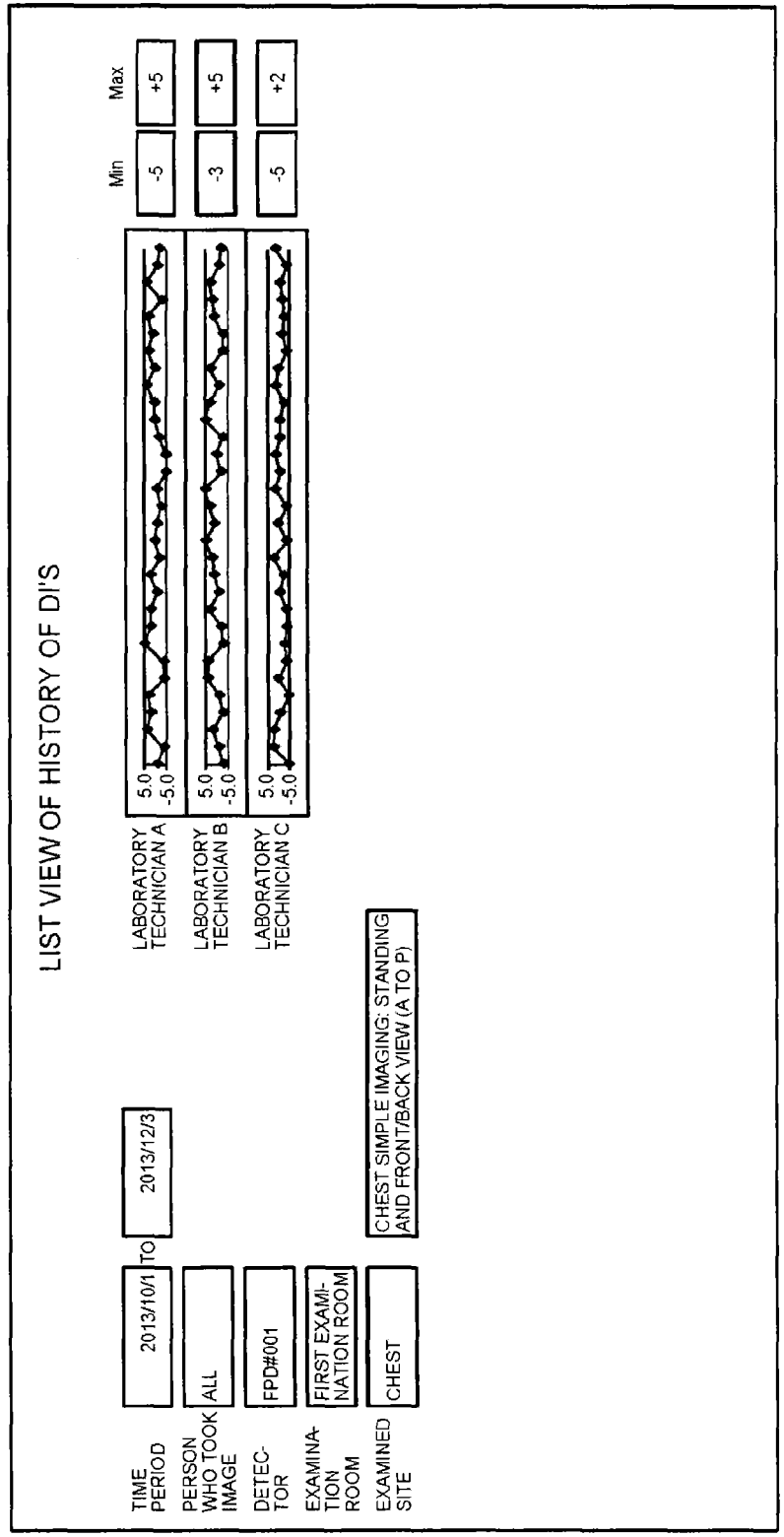
FIG. 7B is a drawing of another example of displaying deviation indices according to the second embodiment.
Figure 7C:
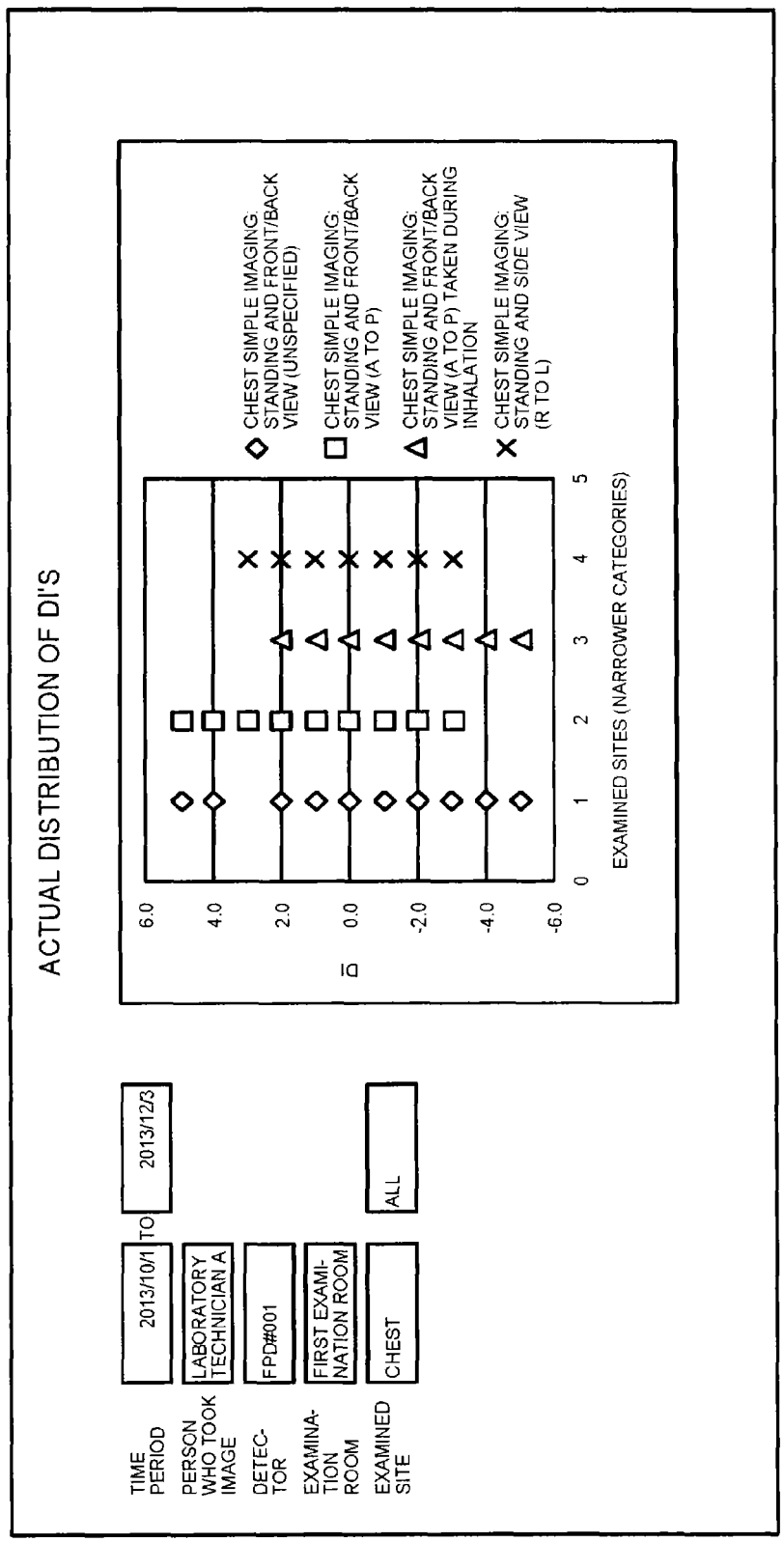
FIG. 7C is a drawing of yet another example of displaying deviation indices according to the second embodiment.

Next, examples of the history information of the deviation indices will be explained, with reference to FIGS. 7A to 7C. FIGS. 7A to 7C are drawings of examples of displaying the deviation indices according to the second embodiment. For example, as illustrated in FIG. 7A, the display controlling unit 211 displays a history of deviation indices during a predetermined time period, for each of the examined sites in the "narrower categories" corresponding to image taking conditions. In one example, the display controlling unit 211 displays a chart indicating a history of deviation indices for each of ten APC items corresponding to the "examined site: chest, ALL", in the "examination room: the first examination room", by using the "detector: FPD #001", among the X-ray images taken by the "person who took the image: laboratory technician A" during the "time period: 2013/10/01 to 2013/12/03". Further, the information about the deviation indices illustrated in FIG. 7A indicates the maximum deviation index value "Max" and the minimum deviation index value "Min" are displayed for each piece of history information, so that it is possible to recognize the fluctuation widths of the deviation indices at a glance.

In this situation, the operator is able to arbitrarily set (narrow down) any of the image taking conditions such as the time period. In other words, it is possible to easily realize the display of the history of deviation indices under various conditions. For example, a laboratory technician may use the displayed information for checking his/her own history or for checking a history of another laboratory technician. Further, it is also possible to check a history of each detector, a history of each examination room, or a detailed history of each examined site.

FIG. 7B illustrates an example in which the display controlling unit 211 causes history information to be displayed for each of different laboratory technicians under mutually the same conditions, by narrowing down the image taking conditions to "time period: 2013/10/01 to 2013/12/03", "person who took the image: ALL", "detector: FPD #001", "examination room: the first examination room", and "examined site: chest; chest simple imaging: standing and front/back view (A to P)". By making a comparison among the laboratory technicians in this manner, it is also possible to understand tendency of the people who take the images.

Further, the history information may be presented not only in the charts in the time series as illustrated in FIGS. 7A and 7B, but also as information indicating a distribution of the deviation indices. For example, as illustrated in FIG. 7C, the display controlling unit 211 may display a chart indicating a distribution of the deviation indices for each of the examined sites in the "narrower categories" by performing the same narrowing-down process as the one illustrated in FIG. 7A. For example, the display controlling unit 211 may realize the display by switching between the information illustrated in FIG. 7A and the information illustrated in FIG. 7C, according to a switching operation performed by the operator via the input unit 22.

Displaying the history information of deviation indices as explained above makes it possible to easily understand non-uniformity among the deviation indices and to efficiently manage the radiation exposure. In this situation, the X-ray diagnosis apparatus 100 according to the second embodiment is also capable of causing corresponding imaged data to be displayed, on the basis of the history information illustrated in FIG. 7A to 7C. More specifically, the X-ray diagnosis apparatus 100 includes a selecting unit configured to select any of the deviation indices displayed by the display unit 23 under the control of the display controlling unit 211, so that the display controlling unit 211 exercises control so as to cause the display unit 23 to display imaging information related to the deviation index selected by the selecting unit. For example, the input unit 22 serving as the selecting unit receives an operation to select one of the deviation indices displayed by the display unit 23 under the control of the display controlling unit 211. Further, the display controlling unit 211 exercises control so as to cause the display unit 23 to display the imaging information related to the deviation index received by the input unit 22.

In the following sections, an example will be explained in which the imaging information is displayed by using the history information of the deviation indices illustrated in FIG. 7A. For example, the operator is able to cause imaging information such as image taking condition data and/or image data to be displayed by performing an operation on the input unit 22 while checking the history information illustrated in FIG. 7A and selecting a piece of history information of which the operator wishes to check the imaging information. (For example, the operator selects one of the deviation indices when he/she assesses that the deviation index is exhibiting an abnormal value.) For example, the operator is able to cause the corresponding imaging information to be displayed by clicking on a data point in the chart illustrated in FIG. 7A or the Max or Min button displayed as buttons on the right side of the chart.

Figure 8:
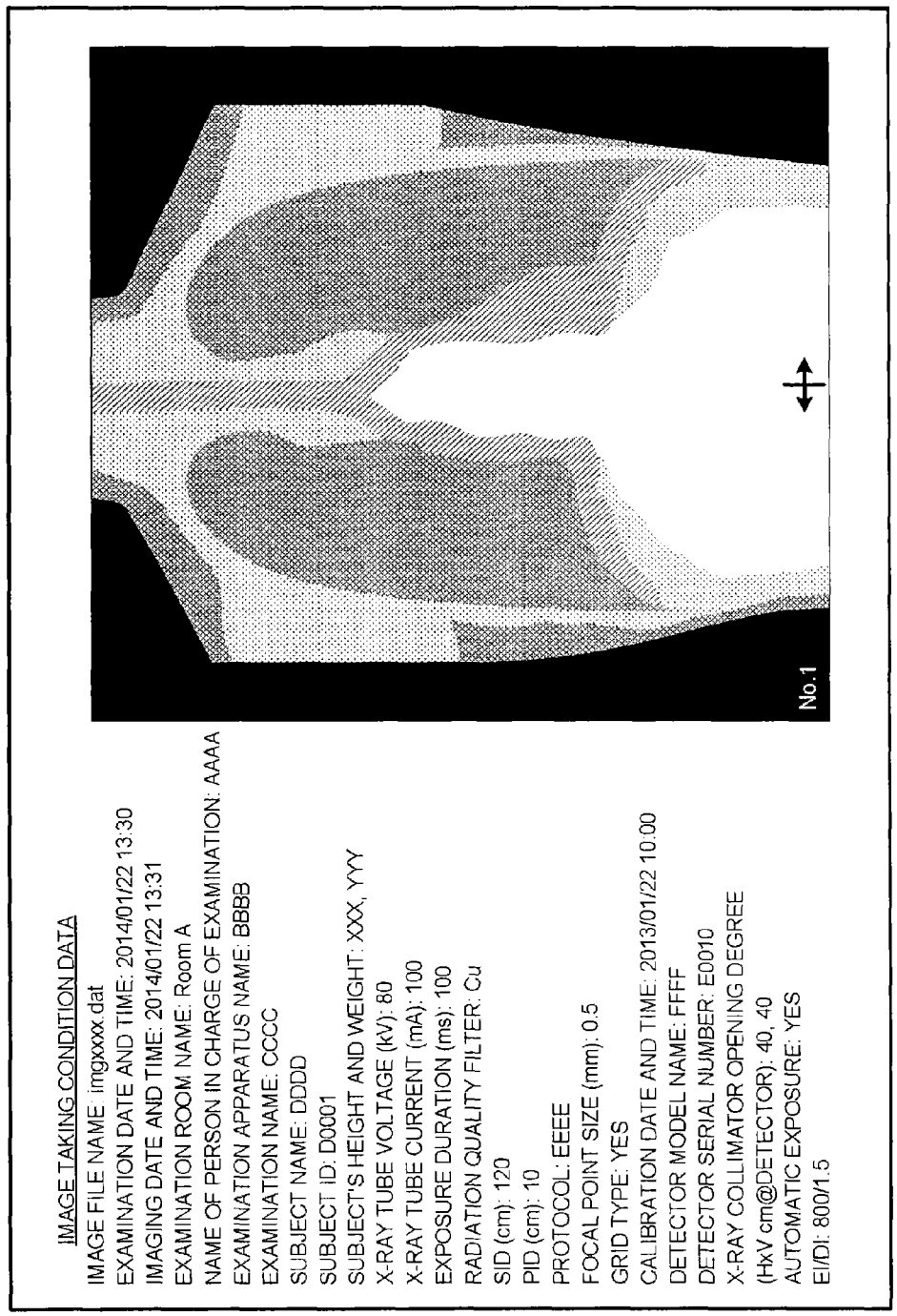
FIG. 8 is a drawing of an example of imaging information according to the second embodiment.

For example, by clicking on the Max button, the operator is able to cause the imaging information to be displayed for an image taking process that corresponds to when the deviation indices exhibited the maximum value. FIG. 8 is a drawing of an example of the imaging information according to the second embodiment. For example, when the operator has selected, via the input unit 22, a piece of history information of which he/she wishes to have the imaging information displayed, the display controlling unit 211 displays image taking condition data of the image taking process that corresponds to the selected piece of history information, as illustrated on the left side of FIG. 8. For example, the display controlling unit 211 causes the display unit 23 to display detailed image taking condition data including the image file name, the date and time of the medical examination, the date and time when the image taking process was performed, the name of the examination room, and the like. Further, when the operator clicks on the image file name via the input unit 22, the display controlling unit 211 causes the X-ray image to be displayed, as illustrated on the right side of FIG. 8.

In the description above, the example is explained in which the display unit 23 is caused to display the imaging information related to the deviation index selected by the operator via the input unit 22. However, possible embodiments are not limited to this example. For instance, the system controlling unit 21 serving as the selecting unit may select one of the deviation indices on the basis of various types of information, so that the imaging information related to the selected deviation index is automatically displayed. In one example, the system controlling unit 21 may exercise control so that the maximum value and the minimum value are selected from among the deviation indices and so that the corresponding imaging information is automatically displayed.

In the description above, the example is explained in which the imaging information is displayed on the basis of the history information illustrated in FIG. 7A. However, it is also possible to cause imaging information to be displayed in a similar manner, on the basis of the history information illustrated in FIG. 7B or FIG. 7C. For example, when using the history information illustrated in FIG. 7B, by clicking on the Max button, the Min button, or a data point in the same manner as in the example in FIG. 7A, it is possible to cause the image taking condition data illustrated in FIG. 8 to be displayed. As another example, when using the history information illustrated in FIG. 7C, by clicking on a data point in the chart indicating the distribution, it is possible to cause the image taking condition data illustrated in FIG. 8 to be displayed. As explained here, by causing the history information of the deviation indices to be displayed and, and also, by further causing the image taking condition data and the image data corresponding to the selected piece of history information to be displayed, it is possible to make it easier to manage the radiation exposure and to easily understand the state of the image taking process corresponding to each of the pieces of history information.

Next, a process performed by the X-ray diagnosis apparatus 100 according to the second embodiment will be explained, with reference to FIGS. 9 and 10. FIGS. 9 and 10 are flowcharts of a procedure in the process performed by the X-ray diagnosis apparatus 100 according to the second embodiment. The process illustrated in FIG. 10 corresponds to the procedure in the process at step S208 in FIG. 9.

As illustrated in FIG. 9, in the X-ray diagnosis apparatus 100 according to the second embodiment, for example, when the system is started up (step S201: Yes), the display controlling unit 211 displays an initial screen (step S202). After that, the display controlling unit 211 receives an operation to move to a utility screen via the input unit 22 and thus displays the utility screen (step S203).

In this situation, by inputting a user ID and a password or the like when performing the operation to move to the utility screen, the operator is authorized that he/she is an operator who is allowed to change any of the target exposure indices. Subsequently, the display controlling unit 211 receives an operation to move from the utility screen to a deviation index management screen via the input unit 22 and thus causes the display unit 23 to display the deviation index management screen (step S204). After that, the display controlling unit 211 causes deviation indices for the APC items in a range selected by the operator to be displayed in a time series as a history (step S205).

Further, when having received an operation to change the range for the deviation indices to be displayed (step S206: Yes), the display information generating unit 214 causes the deviation indices for the APC items in the post-change range to be displayed in a time series as a history. On the contrary, if no changing operation has been received (step S206: No), it is judged whether a selecting operation has been received (step S207). In this situation, when having received a selecting operation (step S207: Yes), the display controlling unit 211 causes data corresponding to the selected deviation index to be displayed (step S208).

On the contrary, if no selecting operation has been received (step S207: No), the display controlling unit 211 judges whether an ending operation has been received (step S209). If no ending operation has been received (step S209: No), the process returns to step S205 so that the display controlling unit 211 continues to display the information. On the contrary, if an ending operation has been received (step S209: Yes), the X-ray diagnosis apparatus 100 ends the process.

As illustrated in FIG. 10, in the X-ray diagnosis apparatus 100 according to the second embodiment, for example, when having received a selecting operation (step S207: Yes), the display controlling unit 211 causes the image taking condition information corresponding to the selected deviation index to be displayed (step S301) and judges whether an image display operation has been received (step S302). In this situation, if an image display operation has been received (step S302: Yes), the display controlling unit 211 displays a corresponding image (step S303).

On the contrary, if no image display operation has been received (step S302: No), the display controlling unit 211 judges whether a data display ending operation has been received (step S304). If no data display ending operation has been received (step S304: No), the display controlling unit 211 continues to display the information. On the contrary, if a data display ending operation has been received (step S304: Yes), the process returns to step S209 so that the display controlling unit 211 judges whether an ending operation has been received.

As explained above, according to the second embodiment, the calculating unit 213 calculates the deviation indices each indicating the difference between the target exposure index indicating the exposure value that is set as a target and the exposure index observed during the image taking process. The display controlling unit 211 exercises control so as to cause the display unit 23 to display the history information of the deviation indices from the predetermined time period. Consequently, the X-ray diagnosis apparatus 100 according to the second embodiment makes it possible to easily check the history information and to efficiently manage the radiation exposure.

The display controlling unit 211 exercises control so as to cause the display unit 23 to display the history of the deviation indices exhibited under each of the image taking conditions during the predetermined time period. Consequently, the X-ray diagnosis apparatus 100 according to the second embodiment makes it possible to check the history of the deviation indices in various situations and to easily understand the status of radiation exposure.

The image taking conditions are represented by one or more selected from among the operator, the detector, the examination room, and the examined site. Consequently, the X-ray diagnosis apparatus 100 according to the second embodiment makes it possible to check the history of the deviation indices in various situations.

The input unit 22 receives the operation to select one of the deviation indices displayed by the display unit 23 under the control of the display controlling unit 211. The display controlling unit 211 exercises control so as to cause the display unit 23 to display the imaging information related to the deviation index received by the input unit 22. Consequently, the X-ray diagnosis apparatus 100 according to the second embodiment makes it possible to display the detailed information about the image taking process during which the selected deviation index was obtained.

Third Embodiment

In a third embodiment, an example will be explained in which a change (correction) candidate for the target exposure index is displayed. In the third embodiment, processes performed by the calculating unit 213 and the display controlling unit 211 are different. In the following sections, the third embodiment will be explained while a focus is placed on the differences.

The calculating unit 213 according to the third embodiment is configured to calculate a change candidate value for a target exposure index, on the basis of the history information of the deviation indices from a predetermined time period. More specifically, the calculating unit 213 according to the third embodiment calculates an average value of the deviation indices included in the history information, as the change candidate value. The display controlling unit 211 according to the third embodiment is configured to exercise control so as to cause the display unit 23 to display the change candidate value calculated by the calculating unit 213. The input unit 22 according to the third embodiment is configured to receive a selecting operation to select deviation indices to be used for the calculation of the change candidate value from among the deviation indices during the predetermined time period.

Figure 11A:
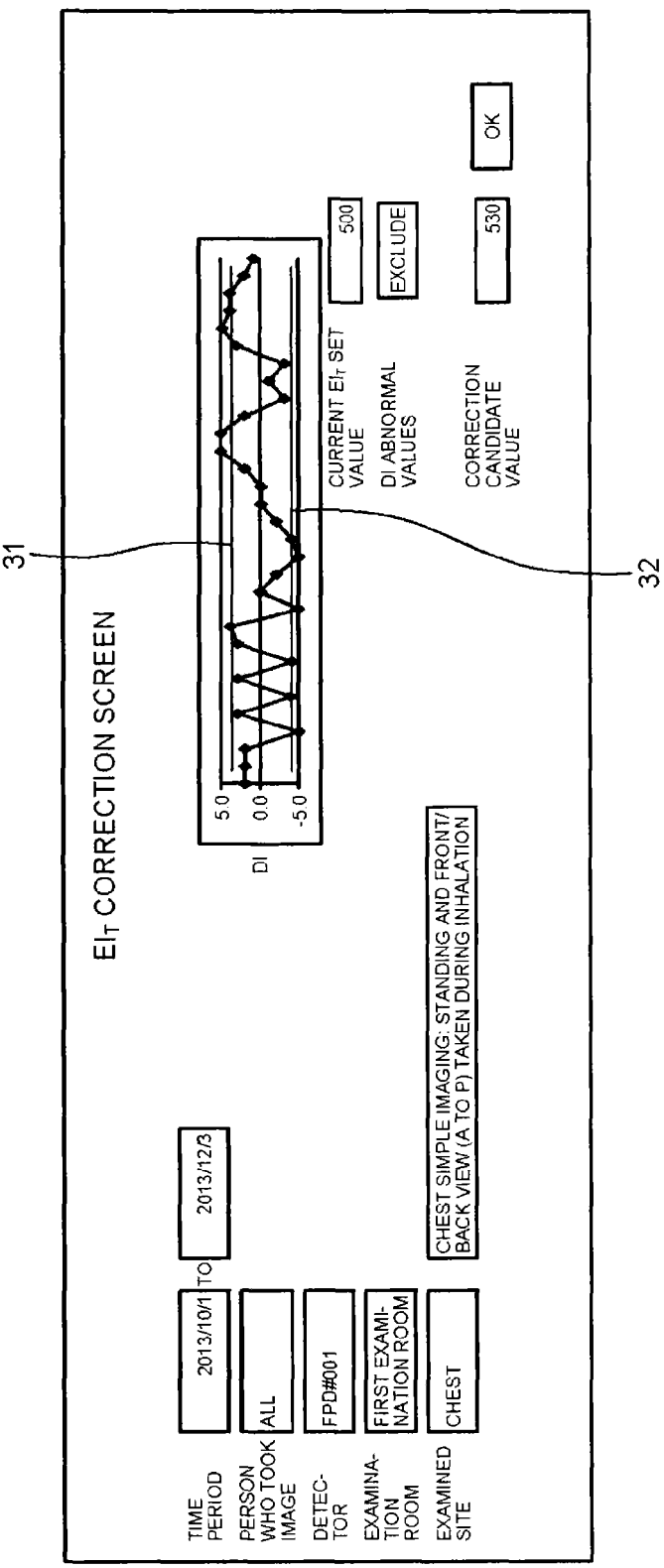
FIG. 11A is a drawing of an example of displaying a change candidate value according to a third embodiment.

FIG. 11A is a drawing of an example of displaying the change candidate value according to the third embodiment. For example, as illustrated in FIG. 11A, the display controlling unit 211 displays a correction image for the target exposure indices. In one example, the display controlling unit 211 displays a "current $EI_T$ set value" and a correction candidate value (a change candidate value), together with a chart indicating a history of deviation indices in a time series. In this situation, the value calculated as the correction candidate value may be, for example, an average value of the deviation indices included in the chart in the time series.

In this situation, it is possible to select one or more values that are not to be used in the calculation of the correction candidate value, from among the deviation indices included in the chart in the time series. For example, the operator selects the values that are not to be used for the calculation of the correction candidate value, by performing an operation on the input unit 22 to set an upper limit value by using a straight line 31 and to set a lower limit value by using a straight line 32 in the chart in the time series. For example, by setting the upper limit value and the lower limit value by sliding the straight line 31 and the straight line 32 over the chart, the operator selects some of the values that are significantly different from other values as abnormal values that are not to be used for the calculation of the correction candidate value and excludes the selected abnormal values from the calculation target by clicking on the "exclude" button illustrated in the drawing.

In this situation, when the "exclude" button has been clicked, the calculating unit 213 calculates a correction candidate value by averaging the deviation indices other than the excluded values, so that the display controlling unit 211 causes the calculated value to be displayed in a correction candidate value area illustrated in the drawing. If the operator has determined that the displayed correction candidate value is appropriate, the operator clicks on the OK button, so that the correction candidate value is set as a new target exposure index. On the contrary, if the operator has determined that the displayed correction candidate value is not appropriate, the operator is able to set a new target exposure index by correcting the correction candidate value via the input unit 22 and clicking on the OK button.

Figure 11B:
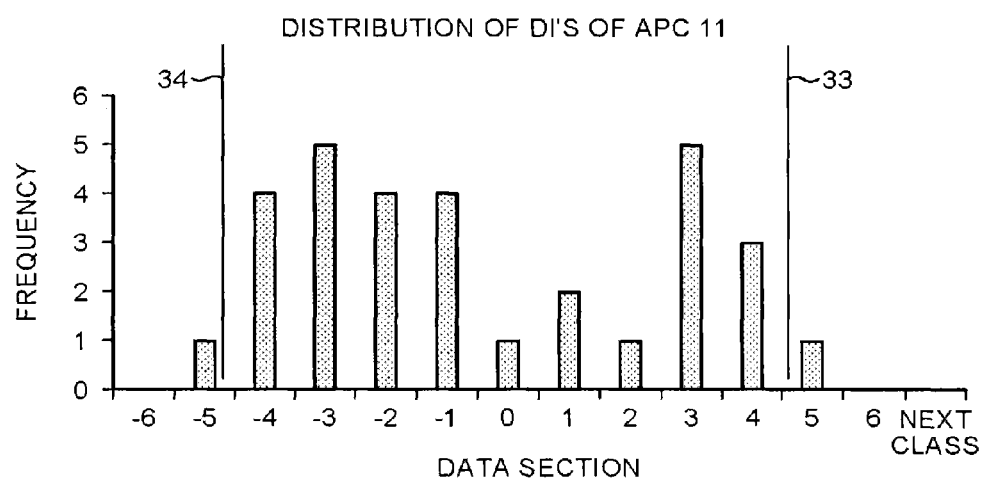
FIG. 11B is a drawing of an example of an image for selecting deviation indices according to the third embodiment.
Figure 11C:
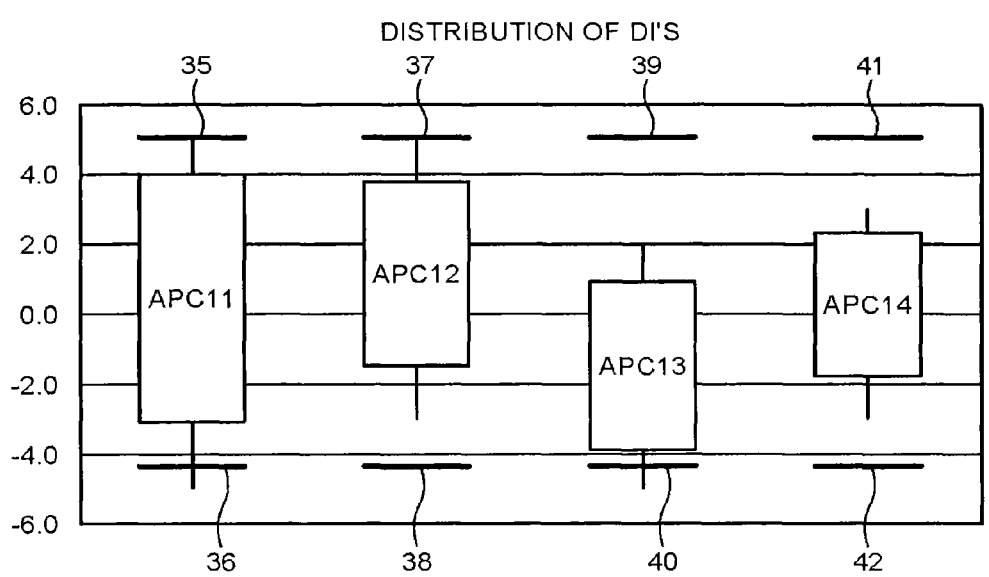
FIG. 11C is a drawing of another example of an image for selecting deviation indices according to the third embodiment.

In this situation, the GUI to set the upper limit value and the lower limit value used for calculating the correction candidate value does not necessarily have to be represented by the straight line 31 and the straight line 32 illustrated in FIG. 11A. It is acceptable to use any of various types of GUIs. For example, it is acceptable to set the upper limit value and the lower limit value by using any of the GUIs illustrated in FIGS. 11B and 11C. FIGS. 11B and 11C are drawings of examples of images for selecting deviation indices according to the third embodiment.

For example, as illustrated in FIG. 11B, the display controlling unit 211 may display the deviation indices in a histogram, so that a data section to be used for the calculation of a correction candidate value is set by using a straight line 33 and a straight line 34. In other words, the data on the right side of the straight line 33 and the data on the left side of the straight line 34 will be excluded.

Alternatively, for example, as illustrated in FIG. 11C, the display controlling unit 211 may cause the display unit 23 to display, at the same time, a plurality of APC items selected by the operator, so that the range for an APC 11 is selected by using a straight line 35 and a straight line 36, the range for an APC 12 is selected by using a straight line 37 and a straight line 38, the range for an APC 13 is selected by using a straight line 39 and a straight line 40, and the range for an APC 14 is selected by using a straight line 41 and a straight line 42. When the range has been selected for each of the APC items, the calculating unit 213 calculates a correction candidate value for each of the APC items, so that the display controlling unit 211 causes the display unit 23 to display the calculated correction candidate values at the same time. The operator inputs a confirmation (clicks on the OK button) for the correction candidate values either individually or collectively, so that the target exposure index for each of the APC items is changed.

When any of the target exposure indices has been changed in the manner described above, the calculating unit 213 stores a change history into the data storage unit 25. FIG. 12 is a drawing of an example of the change history according to the third embodiment. For example, as illustrated in FIG. 12, the calculating unit 213 stores a change history in which an initial setting, change 1, change 2, change 3, change 4, change 5, and the like are kept in correspondence with one another for each of the sites. In this situation, the sites illustrated in FIG. 12 represent the APC items, while the initial setting indicates the target exposure index that was set at the time of the shipment of the X-ray diagnosis apparatus, whereas changes 1 to 5 indicate the change history thereafter.

For example, the calculating unit 213 stores the dates on which a change was made for each of the sites. Further, although not illustrated in the drawing, the calculating unit 213 may further store post-change target exposure indices, in addition to the dates. Although the example illustrated in FIG. 8 only shows the change history of the head and the chest, it is acceptable, in actuality, to arrange a setting so that the change history is displayed on the same screen for all the sites. Alternatively, it is also acceptable to divide the change history so as to be displayed on a plurality of screens, so that the pages are turned by using a "NEXT" button illustrated in the drawing.

The change history stored in the data storage unit 25 is displayed with arbitrary timing in accordance with an operation performed by the operator. For example, it is acceptable to arrange a setting so that a "read" button to read the change history of the target exposure indices is provided on the image taking parameter setting screen corresponding to each of the APC items and so that the change history is displayed when the "read" button is clicked.

Figure 13:
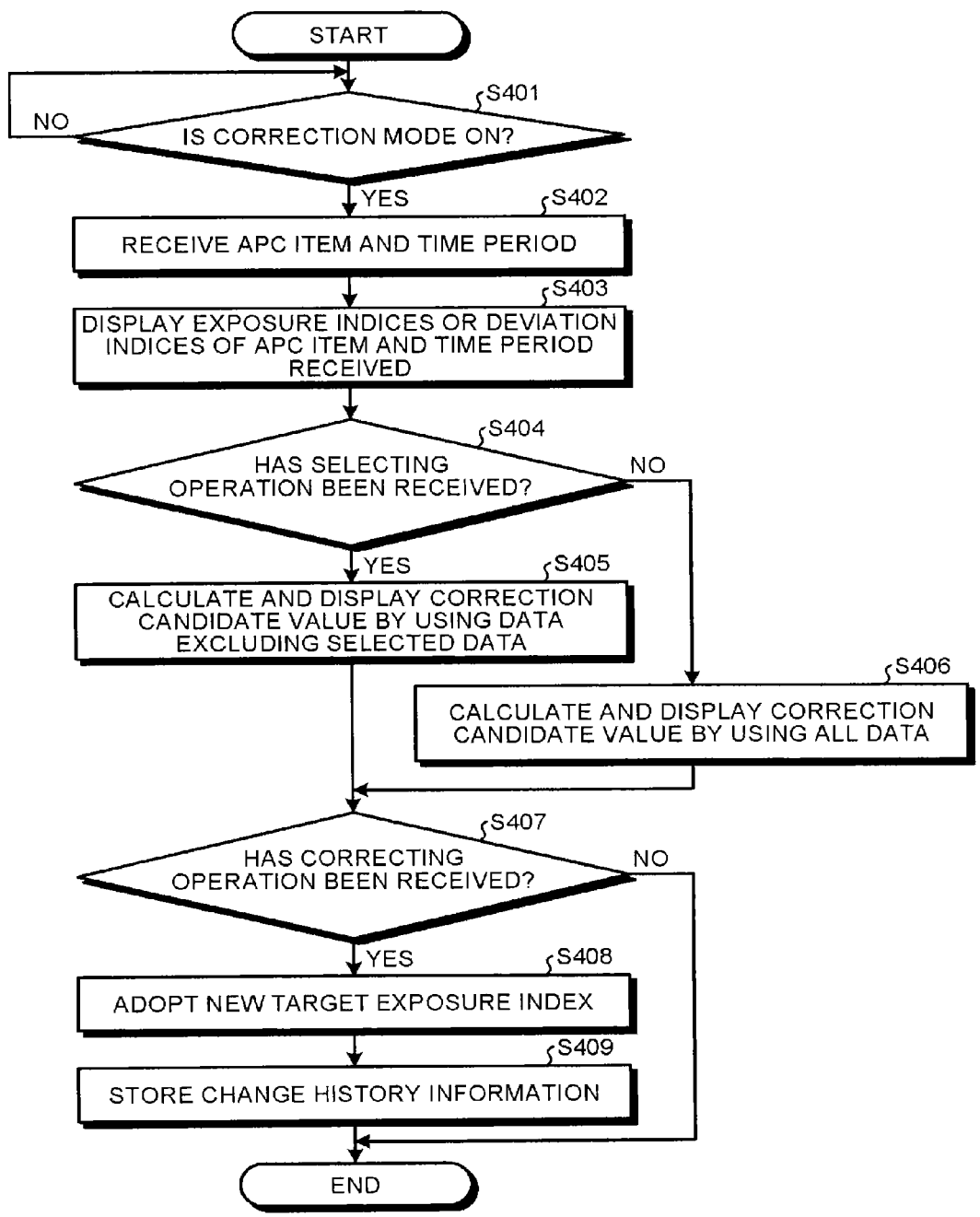
FIG. 13 is a flowchart of a procedure in a process performed by an X-ray diagnosis apparatus according to the third embodiment.

Next, a process performed by the X-ray diagnosis apparatus 100 according to the third embodiment will be explained, with reference to FIG. 13. FIG. 13 is a flowchart of a procedure in the process performed by the X-ray diagnosis apparatus 100 according to the third embodiment. As illustrated in FIG. 13, in the X-ray diagnosis apparatus 100 according to the third embodiment, for example, if a correction mode is on (step S401: Yes), the input unit 22 receives an APC item and a time period being a correction target (step S402). The display controlling unit 211 causes either the exposure indices or the deviation indices corresponding to the APC item and the time period received by the input unit 22 to be displayed (step S403).

In this situation, when an operation to select the data that is not to be used for the calculation of a correction candidate value has been received (step S404: Yes), the calculating unit 213 calculates a correction candidate value by using the data excluding the selected data, so that the display controlling unit 211 displays the correction candidate value (step S405). On the contrary, if no operation to select the data that is not to be used for the calculation of a correction candidate value has been received (step S404: No), the calculating unit 213 calculates the correction candidate value by using all of the data, so that the display controlling unit 211 displays the correction candidate value (step S406).

After that, when a correcting operation (e.g., a click on the OK button) has been received (step S407: Yes), the calculating unit 213 adopts a new target exposure index (step S408) and stores information about the change history into the data storage unit 25 (step S409). On the contrary, if no correcting operation has been received at step S407 (step S407: No), the X-ray diagnosis apparatus 100 ends the process.

As explained above, according to the third embodiment, the calculating unit 213 calculates the change candidate value for the target exposure index, on the basis of the history information of the deviation indices from the predetermined time period. The display controlling unit 211 causes the display unit 23 to display the change candidate value calculated by the calculating unit 213. Consequently, the X-ray diagnosis apparatus 100 according to the third embodiment makes it possible to set the appropriate target exposure index in accordance with the history.

Further, according to the third embodiment, the input unit 22 receives the selecting operation to select the deviation indices that are used for the calculation of the change candidate value, from among the deviation indices during the predetermined time period. The calculating unit 213 calculates the change candidate value by using the deviation indices selected by the selecting operation receiving unit. Consequently, the X-ray diagnosis apparatus 100 according to the third embodiment makes it possible to set the new target exposure index while excluding the abnormal values.

The display controlling unit 211 exercises control so as to cause the display unit 23 to display the change history of the target exposure indices. Consequently, the X-ray diagnosis apparatus 100 according to the third embodiment makes it possible to efficiently manage the exposure.

Fourth Embodiment

The first to the third embodiments have thus been explained. It is, however, possible to carry out the present disclosure in other various modes, besides those described above in the first to the third embodiments.

In the embodiments described above, the example is explained in which at least one selected from the operator, the detector, the examination room, and the examined site is used as the image taking condition; however, possible embodiments are not limited to this example. For instance, the examination facility may be used as an image taking condition. In other words, it is acceptable to calculate and display a deviation index for each facility. In that situation, for example, the exposure management system 1 illustrated in FIG. 1 is further connected to an external network and is configured to calculate and display the deviation index for each facility, by obtaining radiation exposure management information of other facilities.

FIG. 14 is a drawing of an example of displaying deviation indices according to the fourth embodiment. FIG. 14 illustrates an example of a display in which the image taking conditions are narrowed down to "time period: 2013/10/01 to 2013/12/03", "facility: ALL", and "examined site: chest; chest simple imaging: standing and front/back view (A to P)". For example, as illustrated in FIG. 14, the display controlling unit 211 displays a chart in a time series obtained by calculating an average value of the deviation indices for each facility and for each date under mutually the same condition and displays history information indicating the maximum value "Max" and the minimum value "Min" in each of the charts. By causing the history information for each of the facilities to be displayed in this manner, the display controlling unit 211 makes it possible to make a comparison among the facilities and to understand the tendency of radiation exposure in each of the facilities.

In this situation, the history information may be presented not only in the charts in the time series as illustrated in FIG. 14, but also as information indicating a distribution of the deviation indices. Further, the conditions illustrated in FIG. 14 are merely examples. It is also possible to realize a display by switching between pieces of information according to a switching operation performed by the operator via the input unit 22. For example, it is also possible to make a comparison between specific facilities, to change the site of the subject, or to add the type of the detector as an image taking condition.

Further, in the embodiments described above, the example is explained in which the history information of the deviation indices is displayed; however, possible embodiments are not limited to this example. For instance, it is acceptable to display history information of the exposure indices. In that situation, the calculating unit 213 calculates exposure indices by using the conversion table that is stored therein in advance and is used for converting a pixel value into an exposure value, on the basis of information about a representative pixel value obtained by the image information obtaining unit 212. After that, the display information generating unit 214 generates the history information of the exposure indices. Subsequently, the display controlling unit 211 displays the generated history information. In this situation, the display information generating unit 214 is able to generate history information of exposure indices of various types corresponding to different image taking conditions. For example, the display information generating unit 214 is able to generate the history information of the exposure indices that are presented as a chart in a time series, a distribution of the values, and the like.

In the embodiments described above, the examples are explained in which the X-ray diagnosis apparatus 100 performs the various types of processes; however, possible embodiments are not limited to these examples. For instance, the various types of processes may be performed by the workstation 300 or the terminal device 400. In that situation, the workstation 300 or the terminal device 400 has the configuration of the system controlling unit 21 illustrated in FIG. 3 so as to perform the processes described above.

In the embodiments described above, the examples are explained in which the radiation exposure from the X-ray diagnosis apparatus 100 is managed; however, possible embodiments are not limited to these examples. The present disclosure is also applicable to situations where radiation exposure from X-ray Computed Tomography (CT) apparatuses is managed.

Further, the functions of the display controlling unit 211, the image information obtaining unit 212, the calculating unit 213, and the display information generating unit 214 explained in the first to the third embodiments may be realized by using software. For example, the functions of the display controlling unit 211, the image information obtaining unit 212, the calculating unit 213, and the display information generating unit 214 may be realized by causing a computer to execute a program that defines the procedures in the processes that were explained in the embodiments above as being performed by the display controlling unit 211, the image information obtaining unit 212, the calculating unit 213, and the display information generating unit 214. For example, the program is stored in a hard disk, a semiconductor memory element, or the like, so as to be read and executed by a processor such as a Central Processing Unit (CPU), a Micro Processing Unit (MPU), or the like. Further, the program may be distributed as being recorded on a computer-readable recording medium such as a Compact Disk Read-Only Memory (CD-ROM), a Magnetic Optical (MO) disk, a Digital Versatile Disk (DVD), or the like.

As explained above, according to at least one aspect of the embodiments, the exposure management system of the present disclosure makes it possible to efficiently manage the radiation exposure.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An exposure management system comprising: a processing circuitry configured to calculate a deviation index related to a difference between a target exposure index indicating an index of a target exposure value for approximating an exposure value in an X-ray image taking process and an image-taking-period exposure index indicating an index of the exposure value observed during the X-ray image taking process; and cause a display to display history information from a predetermined time period indicating at least one selected from between image-taking-period exposure indices and deviation indices, wherein the processing circuitry is configured to cause the target exposure index and a history of the deviation indices during the predetermined time period to be displayed on a correction screen for correcting the target exposure index based on the history of the deviation indices.

2. The exposure management system according to claim 1, wherein the processing circuitry is configured to select one of the deviation indices displayed by the display and cause the display to display imaging information related to the selected deviation index.

3. The exposure management system according to claim 2, wherein the imaging information includes at least one selected from between the image taking condition and a taken X-ray image.

4. The exposure management system according to claim 1, wherein the processing circuitry is configured to cause the display to display a history of deviation indices exhibited under each image taking condition during the predetermined time period.

5. The exposure management system according to claim 4, wherein the image taking condition is at least one selected from among an operator, a detector, an examination room, an examination facility, and an examined site.

6. The exposure management system according to claim 1, wherein the processing circuitry is configured to cause the display to display, in a list view, the target exposure indices each of which is set for a different one of image taking items of an examined site of which X-ray images are to be taken.

7. The exposure management system according to claim 6, wherein the processing circuitry is configured to cause one or both of absolute values and relative values of the target exposure indices to be displayed in a list view, as the target exposure indices.

8. The exposure management system according to claim 7, wherein the processing circuitry is configured to receive a changing operation to change one or more of the target exposure indices.

9. The exposure management system according to claim 8, wherein the processing circuitry is configured to cause the display to display a change history of the target exposure indices.

10. The exposure management system according to claim 1, wherein the processing circuitry is configured to calculate a change candidate value for the target exposure index on a basis of the history of the deviation indices during the predetermined time period and cause the display to display the calculated change candidate value.

11. The exposure management system according to claim 10, wherein the processing circuitry is configured to receive a selecting operation to select one or more deviation indices that are to be used for calculating the change candidate value from among the deviation indices during the predetermined time period and calculate the change candidate value by using the one or more selected deviation indices.

* * * * *